US012741044B2

(12) United States Patent
Subar

(10) Patent No.: US 12,741,044 B2
(45) Date of Patent: Sep. 22, 2026

(54) METHODS AND APPARATUS FOR CLEANING A MAT

(71) Applicant: Full Tilt Inc., Chicago, IL (US)

(72) Inventor: Steve Subar, Chicago, IL (US)

(73) Assignee: Full Tilt Inc., Chicago, IL (US)

( * ) Notice: Subject to any disclaimer, the term of this patent is extended or adjusted under 35 U.S.C. 154(b) by 70 days.

(21) Appl. No.: 18/584,865

(22) Filed: Feb. 22, 2024

(65) Prior Publication Data

US 2025/0135056 A1 May 1, 2025

Related U.S. Application Data

(63) Continuation-in-part of application No. 17/168,103, filed on Feb. 4, 2021, now abandoned.

(60) Provisional application No. 62/970,081, filed on Feb. 4, 2020.

(51) Int. Cl.

| | |
|---|---|
| ***A61L 2/10*** | (2026.01) |
| ***A61L 2/24*** | (2006.01) |
| ***A61L 2/26*** | (2006.01) |
| ***A63B 6/00*** | (2006.01) |

(52) U.S. Cl.

CPC *A61L 2/10* (2013.01); *A61L 2/24* (2013.01); *A61L 2/26* (2013.01); *A61L 2202/11* (2013.01); *A61L 2202/121* (2013.01); *A61L 2202/14* (2013.01); *A63B 6/00* (2013.01)

(58) Field of Classification Search

CPC ..... A61L 2/10; A61L 2/24; A61L 2/26; A61L 2202/11; A61L 2202/14; A61L 2202/17; A61L 2202/121; A61L 2202/122; A63B 6/00; A63B 21/4037; A63B 2225/30; B08B 3/022; B08B 1/20; B08B 7/0057; G07F 17/20

See application file for complete search history.

(56) References Cited

U.S. PATENT DOCUMENTS

| | | | | |
|---|---|---|---|---|
| 4,194,837 A * | 3/1980 | Tani | G03B 27/6257 | 355/75 |
| 4,926,215 A * | 5/1990 | Rank, Jr. | G03B 27/10 | 355/99 |
| 5,223,229 A * | 6/1993 | Brucker | B01J 3/03 | 422/112 |
| 8,028,365 B2 * | 10/2011 | Field | A47L 11/4088 | 15/230.14 |

(Continued)

FOREIGN PATENT DOCUMENTS

WO WO-2010089766 A1 * 8/2010 ............. B65H 9/002

*Primary Examiner* — Wyatt A Stoffa
*Assistant Examiner* — Jing Wang
(74) *Attorney, Agent, or Firm* — INCUBATE IP; Randy R. Micheletti

(57) ABSTRACT

Methods and apparatus for cleaning a mat are disclosed. The disclosed process receives a user identifier, such as a phone number and/or PIN, at a mat cleaner from a user. The mat cleaner then accepts a mat, such as a yoga mat, form the user and conveys the mat through the mat cleaner. Various guides and sensors are employed to facilitate straight insertion and smooth conveyance of the mat through the mat cleaner. As the mat is conveyed, the mat is illuminated with ultraviolet light and sprayed with a recirculated cleaning solution. The mat cleaner includes a sensor, such as a float switch, to facilitate determination of the circulated cleaning solution level.

13 Claims, 15 Drawing Sheets

(56) References Cited

U.S. PATENT DOCUMENTS

| | | | | |
|---|---|---|---|---|
| 8,479,342 | B2 * | 7/2013 | Benson | B08B 1/20 |
| | | | | 15/40 |
| 8,779,391 | B2 * | 7/2014 | Flaherty | A61L 2/24 |
| | | | | 250/461.1 |
| 9,662,682 | B2 * | 5/2017 | Perrier | B08B 1/12 |
| 10,223,681 | B2 * | 3/2019 | Cashman | G16H 40/20 |
| 2013/0270384 | A1 * | 10/2013 | Akpan | B65H 26/00 |
| | | | | 242/534 |
| 2014/0020723 | A1 * | 1/2014 | Murphy | B08B 1/20 |
| | | | | 134/104.2 |
| 2017/0189947 | A1 * | 7/2017 | Butler | A61L 2/00 |
| 2021/0023248 | A1 * | 1/2021 | Townsend | A61L 2/10 |
| 2021/0339291 | A1 * | 11/2021 | Allan | B08B 3/022 |

* cited by examiner

METHODS AND APPARATUS FOR CLEANING A MAT

PRIORITY CLAIM

This application is a continuation-in-part of U.S. patent application Ser. No. 17/168,103, filed on Feb. 4, 2021, which claims priority to U.S. Provisional Patent Application Ser. No. 62/970,081, filed on Feb. 4, 2020, the entire contents of each of which are incorporated herein by reference and relied upon.

FIELD

The present disclosure relates in general to processing mats, and, in particular, to methods and apparatus for cleaning a mat using a mat processing device.

BACKGROUND

Traditionally, users of exercise mats, such as yoga mats, clean and disinfect their mats manually. For example, after a yoga session, a participant may spray his/her mat with a cleaner and wipe the mat down with a towel. However, this method is cumbersome and often ineffective. Mat processing devices have been used to attempt to overcome these limitations of manual mat cleaning. However, current mat processing devices, and the associated methods of using these mat processing devices, lack certain improvements disclosed herein. For example, current mat processing devices suffer from jammed mats. In addition, current mat processing devices do not sufficiently and efficiently clean the mats they process.

A need remains for devices that effectively and reliably clean and roll mats of various sizes and thicknesses.

SUMMARY

Methods and apparatus for cleaning a mat are disclosed. The disclosed process receives a user identifier, such as a phone number and/or PIN, at a mat cleaner from a user. The mat cleaner then accepts a mat, such as a yoga mat, form the user and conveys the mat through the mat cleaner. Various guides and sensors are employed to facilitate straight insertion and smooth conveyance of the mat through the mat cleaner. As the mat is conveyed, the mat is illuminated with ultraviolet light and sprayed with a recirculated cleaning solution. The mat cleaner includes a sensor, such as a float switch, to facilitate determination of the circulated cleaning solution level.

In some embodiments, the present disclosure provides a device for cleaning a mat, the device comprising: an inlet feed system configured to draw a mat into the device; an ultraviolet irradiation module configured to sanitize the mat; a rolling module configured to roll the sanitized mat into a roll; and an automatic door actuator configured to selectively prevent a door from opening and to open the door.

OBJECTS OF THE DISCLOSED TECHNOLOGIES

It is one object of the disclosed technologies to provide a device that reliably feeds, sanitizes, and rolls a mat.

It is another object of the disclosed technologies to sanitize mats having a variety of dimensions and thicknesses using only UV irradiation.

It is another object of the disclosed technologies to automatically roll mats having a variety of dimensions and thicknesses while reducing rolling anomalies such as telescoping.

It is another object of the disclosed technologies to automatically roll mats whether dry or damp while reducing rolling anomalies such as telescoping.

DETAILED DESCRIPTION

Figure 1:
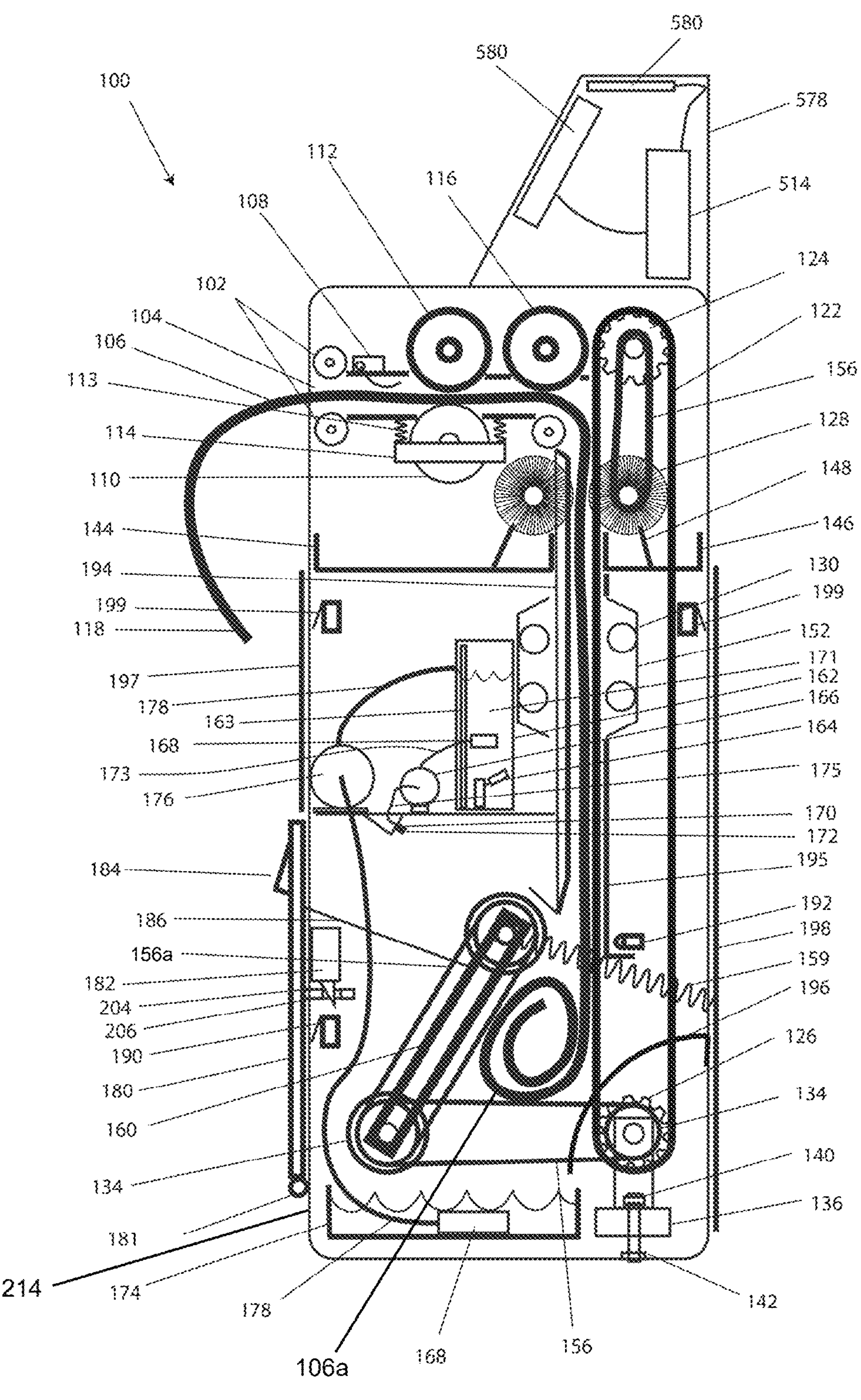
FIG. 1 is a side view of an example mat cleaner consistent with one embodiment of the present disclosure.

FIG. 1 illustrates a side view of an example mat cleaner 100. In this example, the mat cleaner 100 includes one or more entrance guide rollers 102, which are located at or near the top and bottom of an insertion slot 104. The entrance guide rollers 102 rotate upon contact with a mat 106 to allow the mat 106 to be inserted into the insertion slot 104 without getting stuck on a surface of the mat cleaner 100 due to friction.

Once the mat 106 contacts one or more activation switches 108 located near the front of the insertion slot 104, the mat cleaner 100 is activated, thereby causing one or more idler rollers 110 and one or more front driver rollers 112 to pull the mat 106 into the mat cleaner 100. The activation switches 108 are structured to prevent the mat 106 from being inserted in a crooked orientation. Ends of the idler roller 110 are connected to one or more spring 113 loaded tensioner brackets 114, allowing the idler roller 110 to dynamically apply a predefined pressure to convey the mat 106 in accordance with dimensions of that particular mat 106. One or more rear driver rollers 116 push the tail end 118 of the mat 106 into a conveyor subsystem 120.

The conveyor subsystem preferably includes one or more vertically aligned conveyor chains 122 and/or belts that are threaded around one or more upper sprockets 124 and one or more lower sprockets 126. The upper sprockets 124 and lower sprockets 126 cooperate to move the conveyor chains 122. When a mat 106 contacts the conveyor chains 122, the movement causes the mat 106 to be conveyed vertically in the mat cleaner 100 through one or more brushes 128 and/or UVC lamps 130.

A bottom shaft 132 of the conveyor subsystem 120 houses the lower sprockets 126 and pulleys 134, which are installed into a main tensioner bracket 136. The main tensioner bracket 136 is preferably mounted to a frame using chain tensioner bolts 140. Tightening down these chain tensioner bolts 140 effectively causes the height of the main tensioner bracket 136 to change, which determines a conveyor chain tension. Once the conveyor chains 122 are properly tensioned, a nut 142 is preferably placed on the ends of the chain tensioner bolts 140 to help ensure that the chain tensioner bolts 140 will not loosen and cause the main tensioner bracket 136 to move. Because the main tensioner bracket 136 may be subjected to significant stress, support measures are preferably included to stabilize the main tensioner bracket 136, such as L-brackets, thick shims that fasten the bracket to the frame, and/or any other suitable bracket stabilization means.

The brushes 128 (e.g., roller brushes) preferably remove dirt and/or debris from both sides of the mat 106 substantially simultaneously. The dirt and/or debris may then be collected in a front dust bin 144 and/or a rear dust bin 146 after being removed from the bristles of the brushes 128 via brush combs 148.

A UVC system includes one or more UVC lamps 130 to illuminate the mat 106 with the radiation necessary to eradicate pathogens. The pathogens are preferably eradicated on both sides of the mat 106 simultaneously. One or more UVC lamp covers 152 house the UVC lamps 130 along and prevent harmful radiation from affecting users of the mat cleaner 100. There exists a reflective surface on the inside of the lamp covers in order to magnify the UVC light dosage that is applied to the mat.

When a mat 106 exits the conveyor subsystem 120, the mat 106 hits a first series of round belts 156, **156*a* that make up a rolling subsystem 158. The round belts 156,156*a* preferably sit in grooves of adjacent pulleys 134 that are preferably located on an inner door arm 160, and a lower conveyor shaft. The round belts 156, 156*a* make contact with rubber bands that sit in the grooves of the pulleys 134 to prevent slippage of the round belts 156, 156*a*. The round belts 156,156*a* can be made of varying lengths, materials (polyurethane rubber, rubber, etc.), and designs (round belts, timing belts, etc.). The round belts 156,156*a*** are preferably of a suitable flexibility, while still maintaining an ability to rotate due to the drive chain control. A person of ordinary skill in the art will readily appreciate that compatible pulleys and/or sprockets may be selected for different belt types and lengths.

As the pulleys 134 and round belts 156, **156*a* rotate, the mat 106 is pulled along the first set of round belts 156 to the second set of round belts 156*a* located on an inner door arm 160 and a rolled mat 106*a* begins forming. The rolled mat 106*a* continues increasing in diameter as the mat 106*a* continues being fed through the mat cleaner 100. Due to a spring mechanism 159 of the inner arm door 160 and flexibility of the round belts 156, 156*a*, the angle of the inner arm door 160** is able to adjust to the increasing mat thickness while keeping a tight roll.

A hydraulics subsystem preferably sprays both sides of the mat 106 with an all-natural cleaning solution. A HOCL compatible reservoir 162 houses the cleaning solution. The reservoir 162 is composed of fittings for the inlets, a fitting for the outlet, a fluid level sensor 163, and a lid. All of these components are preferably connected to the reservoir 162 with a watertight seal. For example, a thread seal, O-rings, nuts, or any combination thereof. The reservoir 162 preferably includes an inlet for air to prevent any pressure build up. This can be accomplished with an air inlet fitting and/or holes located on the reservoir lid. Additionally, an electronic float switch 164 located inside the reservoir 162 may automatically detect if the cleaning solution needs to be refilled. This data is preferably transmitted to a cloud-based application to notify one or more entities to refill the cleaning solution 171.

Electronically controlled spray pumps 166 extract the cleaning solution 171 from the reservoir 162 through a nozzle strainer 168 to prevent small particles from clogging the spray nozzle 170 openings. For example, the strainer 168 may be a mesh bag and/or a disk filter. The strainer 168 may be located inside of the reservoir 162 or the strainer 168 may be directly connected in a line before the solution reaches the spray nozzles 170. The filtered cleaning solution 171 travels from the spray pump inlet 173, to the spray pump outlet 175, to the spray nozzles 170 through a series of tubes that are connected using fittings, such as but not limited to john guest fittings. The cleaning solution 171 then exits the spray nozzle 170 openings and is sprayed onto the mat 106 to serve as a secondary sanitizing method. The spray nozzles 170 are preferably installed at a predetermined height, location, and angle, so that the spray nozzles 170 spray both sides of the mat 106 when the mat 106 is being rolled. A cone 172 of the spray nozzles 170 may have a predetermined angle that allows some or all of surface of the mat 106 to be sprayed with a suitable spray amount.

A drip tray 174 preferably collects some or all of any overspray that occurs. The water pump 176 pulls this overspray through the strainer 168 and into a recirculation line 178. The strainer 168, which may be a mesh bag and/or a disk filter, prevents debris from being introduced into the hydraulics system. The recirculation line 178 preferably sits predominantly flat on the drip tray 174 in order to suction a sufficient quantity of overspray. This can be accomplished by fastening the recirculation line 178 (e.g., with tape and/or a fitting) to the drip tray 174. Alternatively, the recirculation line 178 can be kept relatively flat by weighing it down (e.g., with a heavy plate or rocks). The filtered overspray is then funneled back into the reservoir 162 through the recirculation line 178. Recirculating the cleaning solution 171 allows the hydraulic subsystem 177 to operate as a maintenance free closed loop.

The door 180 preferably has material etched out, so light is visible through the front in order to draw attention to the mat cleaner 100 to maximize utilization. The etch can be of the logo, any shapes, or lettering to provide users with visibility that the UV light 130 is on. If this etch is located on a panel that allows spray to exit the mat cleaner 100, the etch is preferably covered with a clear backing.

The door 180 preferably includes lock brackets on each side that interact with solenoid locks 182 to keep the door 180 closed. For safety reasons, the door 180 on hinges remains locked until a cleaning cycle is complete, so hands are not inserted into the mat cleaner 100 when it is operating.

A handle 184 located on the door 180 enables a user to open the door 180. A steel cable 186 connects the inner door arm 160 to the door 180 allowing for both the inner door arm 160 and the door 180 to open automatically, creating an unobstructed opening for mat 106 retrieval.

An electronics control box 188 preferably includes a printed circuit board (PCB), microprocessor, input devices (e.g., sensors, microswitches, touch screen display, etc.) and output devices (e.g., relays, motor, pumps, lights, touch screen display, etc.) to control operation of the mat cleaner 100. The PCB supports and electronically controls the electro-mechanical components that make up the mat cleaner 100. Additionally, the PCB may gather and record data from the input signals it receives. The PCB preferably includes a microcontroller and software and connects to a Wi-Fi network and a cellular network.

A door switch 190 located between the door 180 and the frame is able to determine whether the door 180 is opened or closed. When the door 180 is open, and not making contact with the door switch 190, the mat cleaner 100 may prompt an error message indicating the door 180 is open. Similarly, if the door switch 190 detects the door 180 has not been opened after a completed cleaning cycle, the user may be warned that a mat 106 remains in the mat cleaner 100.

Aside from controlling the systems within the mat cleaner 100, the electronics control box 188 may include a cellular antenna that allows the mat cleaner 100 to communicate with a cellular network. The cellular connection allows for pushing firmware updates over the air along with reporting any data pertaining to usage or faults.

When a mat 106 is conveyed through the mat cleaner 100 and the mat 106 passes an optical sensor 192, the hydraulics subsystem 177 is activated. Similarly, the hydraulics subsystem 177 is deactivated when the tail end of the mat 106 passes the optical sensor 192. If the optical sensor 192 does not detect a mat 106 after a predetermined amount of time once the cleaning cycle has begun, the mat cleaner 100 may indicate a mat jam and the mat 106 may be automatically reversed.

The mat cleaner 100 preferably includes a front plate 194 and a back plate 195 to keep the mat 106 flat when the mat 106 is being conveyed through the mat cleaner 100. The front plate 194 and the back plate 195 are preferably structured to reduce the amount of surface friction and unnecessary openings in locations where a mat 106 may make contact with the plates 194, 195. The low friction plate helps prevent a mat 106 from jamming by providing a low friction, curved surface for the mat 106 to be conveyed along.

Guide round belts 156 cause a horizontally inserted mat 106 to curve downwards and contact the vertical conveyor subsystem. One or more sprocket covers 196 help prevent a mat 106 from getting stuck between the conveyor chains 122 and the teeth of the lower sprockets.

In addition to acting as an external body of the mat cleaner 106, the front cover 197 and the rear cover 198 may be used as maintenance access panels. When a panel is removed, contact switches 199 located behind the front cover 197 and/or the rear cover 198 preferably deactivate. This may prompt an error message along with disabling both the motor and the UVC lamps.

Figure 2:
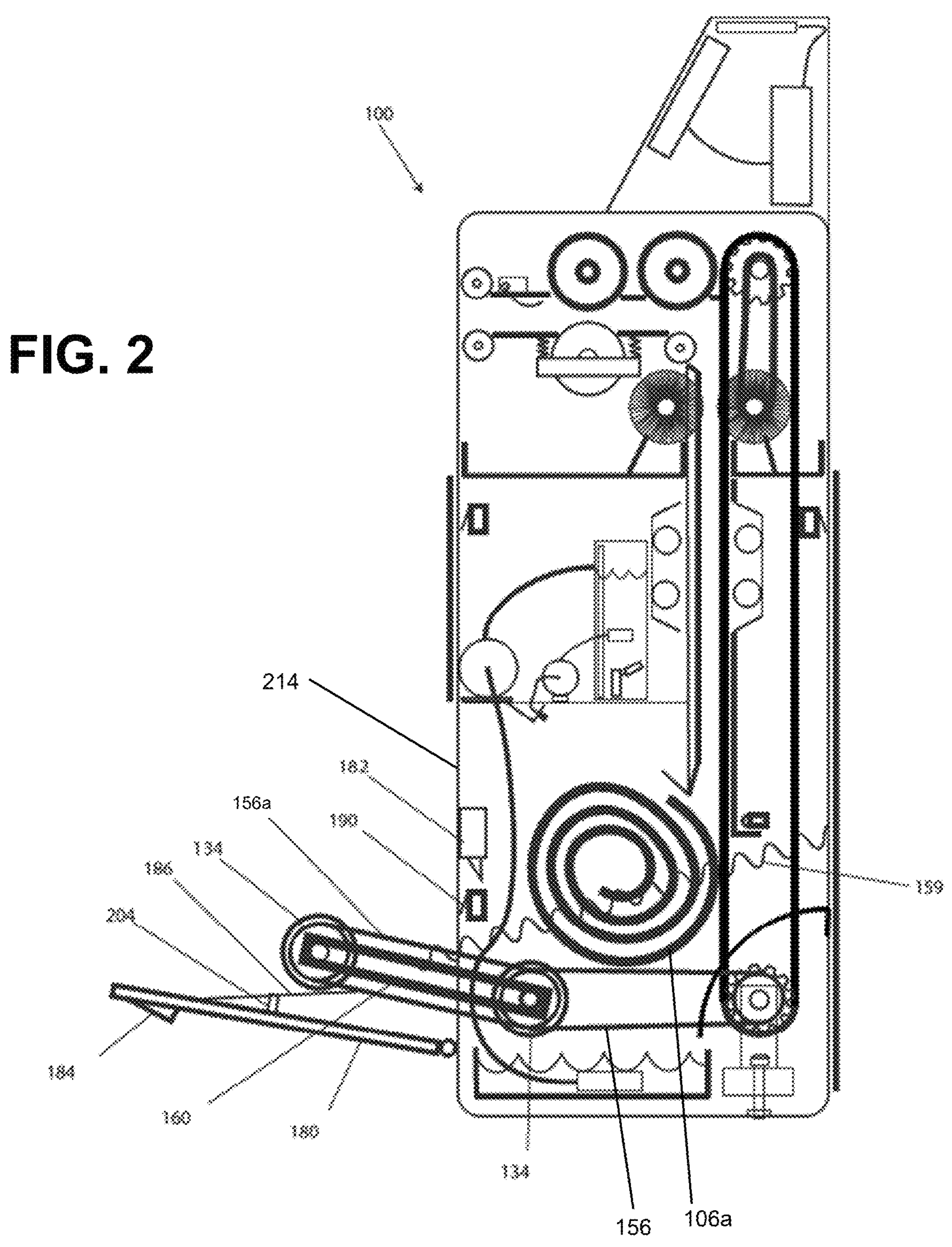
FIG. 2 is another side view of the example mat cleaner with the door of the mat cleaner in an open position.

FIG. 2 illustrates another side view of the example mat cleaner 100 with the door of the mat cleaner 106 in an open position. In this example, the inner door arm 160, made up of one or more pulleys 134 and one or more round belts 156, causes the mat 106 to roll up tightly.

Once a cleaning cycle is complete, one or more solenoid locks 182 deactivate and retract from an opening 204 in the lock brackets 206. This retraction causes the door 180 to open automatically, so users know where to remove the mat 106 from. A handle 208 enables users to open the door 180. A steel cable 210 connects the inner door arm 160 to the door 180 allowing the inner door arm 160 and the door 180 to both open automatically, creating an unobstructed opening for mat retrieval.

The door switch 190 located between the door 180 and the frame 214 is able to facilitate determination of whether the door 180 is opened or closed. When the door 180 is open, and not contacting the door switch, the mat cleaner 100 preferably generates an error message indicating the door 180 is open. Similarly, if the door switch 190 indicates that the door 180 has not been opened after a completed cleaning cycle, the mat cleaner 100 preferably warns the user that there a mat 106 remains in the machine.

Figure 3:
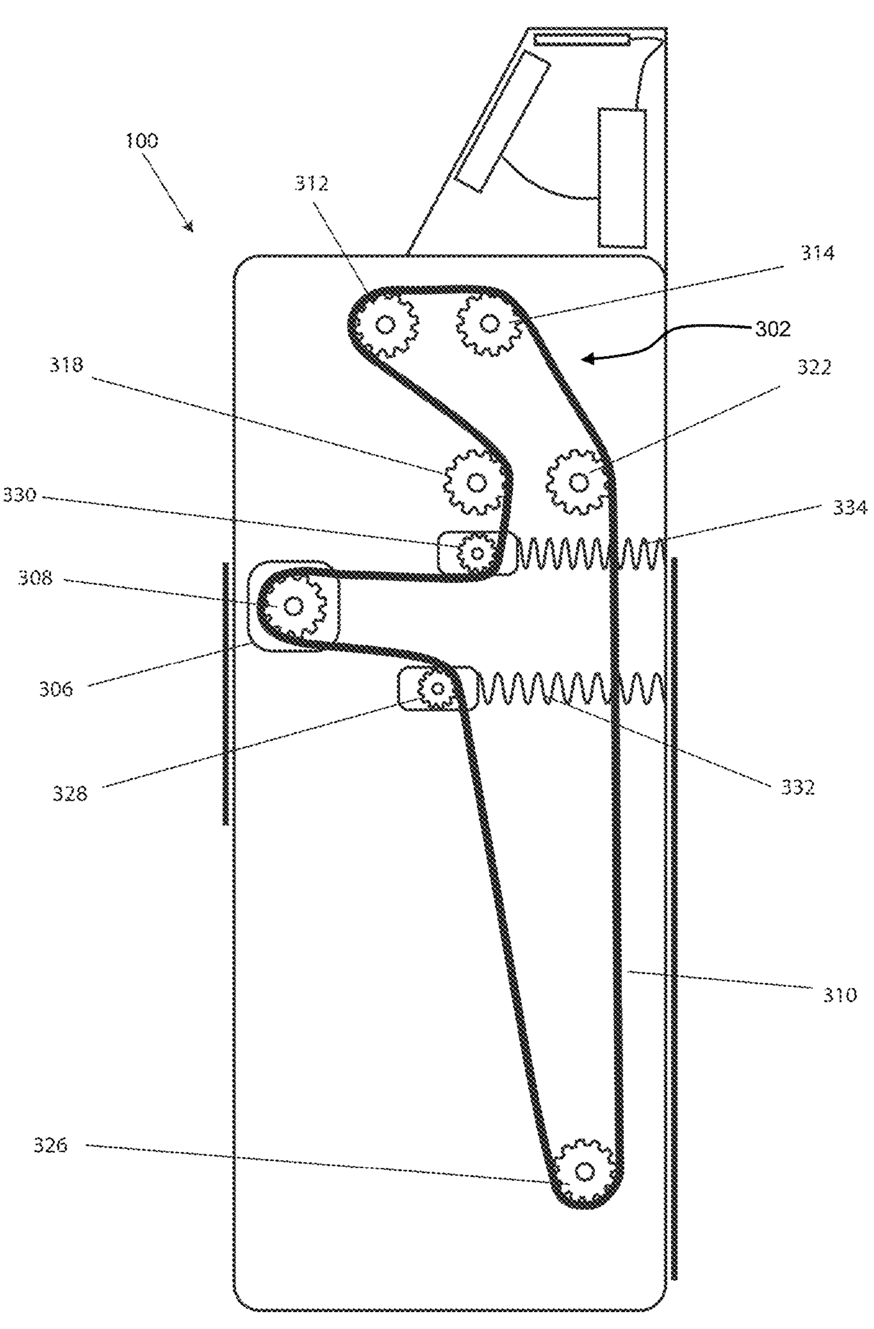
FIG. 3 is yet another side view of the example mat cleaner highlighting the drive train of the mat cleaner.

FIG. 3 illustrates yet another side view of the example mat cleaner 100 highlighting the drive train 302 of the mat cleaner 106. Once the activation switches 108 are engaged by contacting a mat 106, a stepper motor 306 is activated. The motor sprocket 308 installed on the shaft of the stepper motor 306 controls the drive chain 310 that drives the system. The drive chain 310 is threaded around the front drive sprocket 312 and the rear drive sprocket 314, which control the driver rollers 112,116. The drive chain 310 is also threaded around a front brush roller sprocket 318, which controls the front brush 320. The drive chain 310 is also threaded around a rear brush roller sprocket 322, which controls the rear brush 324. The drive chain 310 is also threaded around the mat rolling mechanism sprocket 326, which controls the rolling of the mat 106 along with driving the conveyor system.

The drive chain 310 is also threaded around the teeth of a forward tensioner sprocket 328 and a reverse tensioner sprocket 330. The forward tensioner sprocket 328 is connected to a forward tension spring 332 and the reverse tensioner sprocket 330 is connected to a reverse tension spring 334. These spring mechanisms allow the forward tensioner sprocket 330 and the reverse tensioner sprocket 330 to move dynamically and adjust chain tension based on torque applied to convey the mat 106, mat dimensions and mat material. An alternative method, effectively allowing the drive chain 310 to handle changes in the tension, employs tensioner sprockets placed between two sides of the drive chain 310. In this embodiment, the tensioner sprockets help prevent the drive chain 310 from jumping teeth when tension changes occur.

Figure 4:
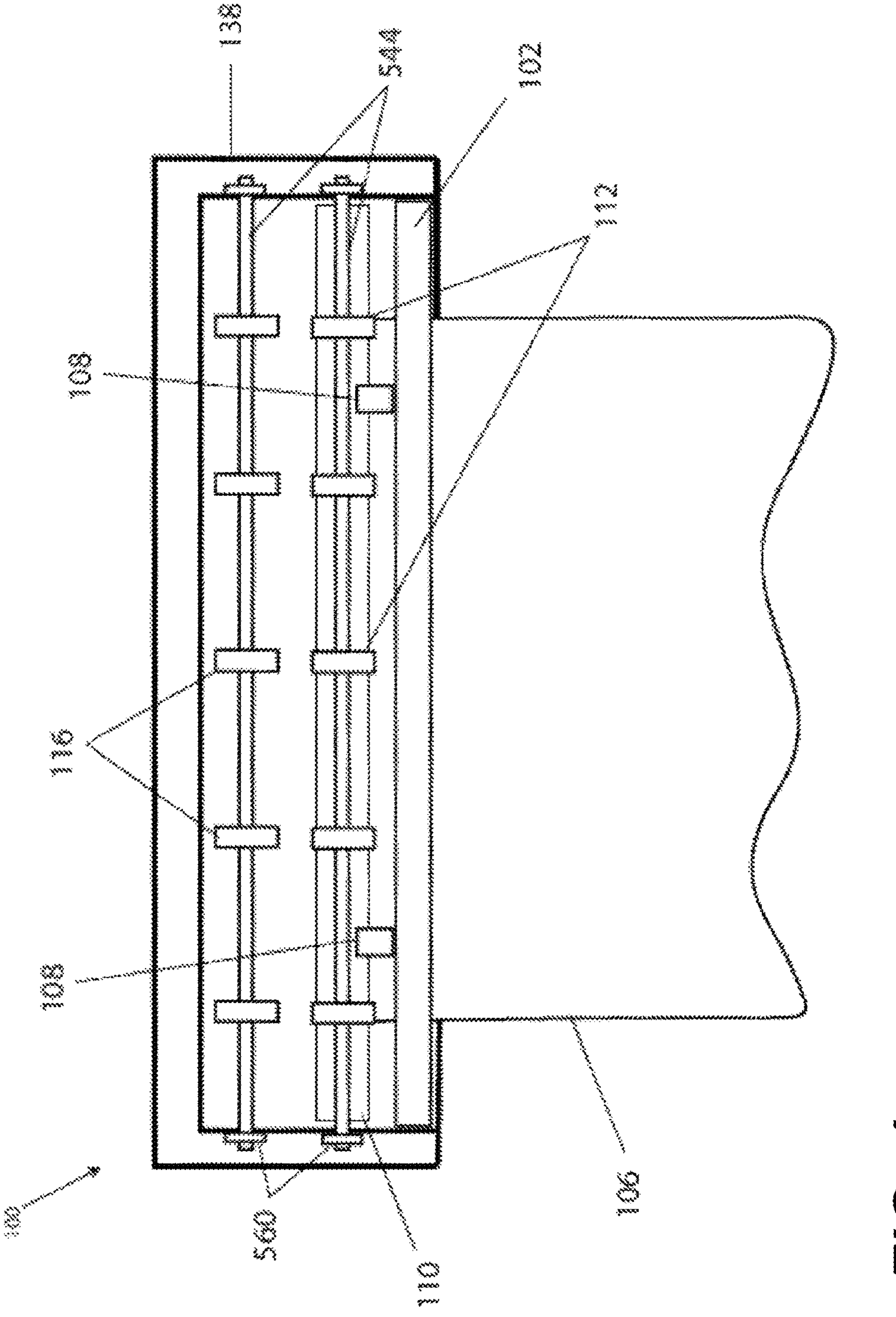
FIG. 4 illustrates a top view of the example mat cleaner.

FIG. 4 illustrates a top view of the example mat cleaner 100. The driver rollers 112,116 exist on shafts located within the housing of the mat cleaner 100. The end of each shaft is installed into a flange bearing 560 to allow for a smooth rotation when driven by the drive chain 310. The driver rollers 112,116 can have a flat or grooved surface and they can be made of any high friction material, such as rubber. The driver rollers 112,116 can either be made up of multiple individual traction rollers or one solid roller.

Once a mat 106 contacts one or more activation switches 108 located near the front of the insertion slot 104, the mat cleaner 100 is preferably activated causing an idler roller 406 and front driver roller 112 to pull the mat 106 into the mat cleaner 100. The activation switches 108 are structured to prevent the mat 106 from being inserted in a crooked orientation.

The rear driver rollers 116 push the tail end of the mat 106 to the conveyor subsystem 120. The idler roller 406 is preferably a solid pipe that is able to rotate freely and is preferably be made of a material with a low friction coefficient, such as PVC. The idler roller 406 may have a mechanism in place that allows the idler roller 406 to automatically adjust the idler roller height for any different mat thicknesses.

Figure 5:
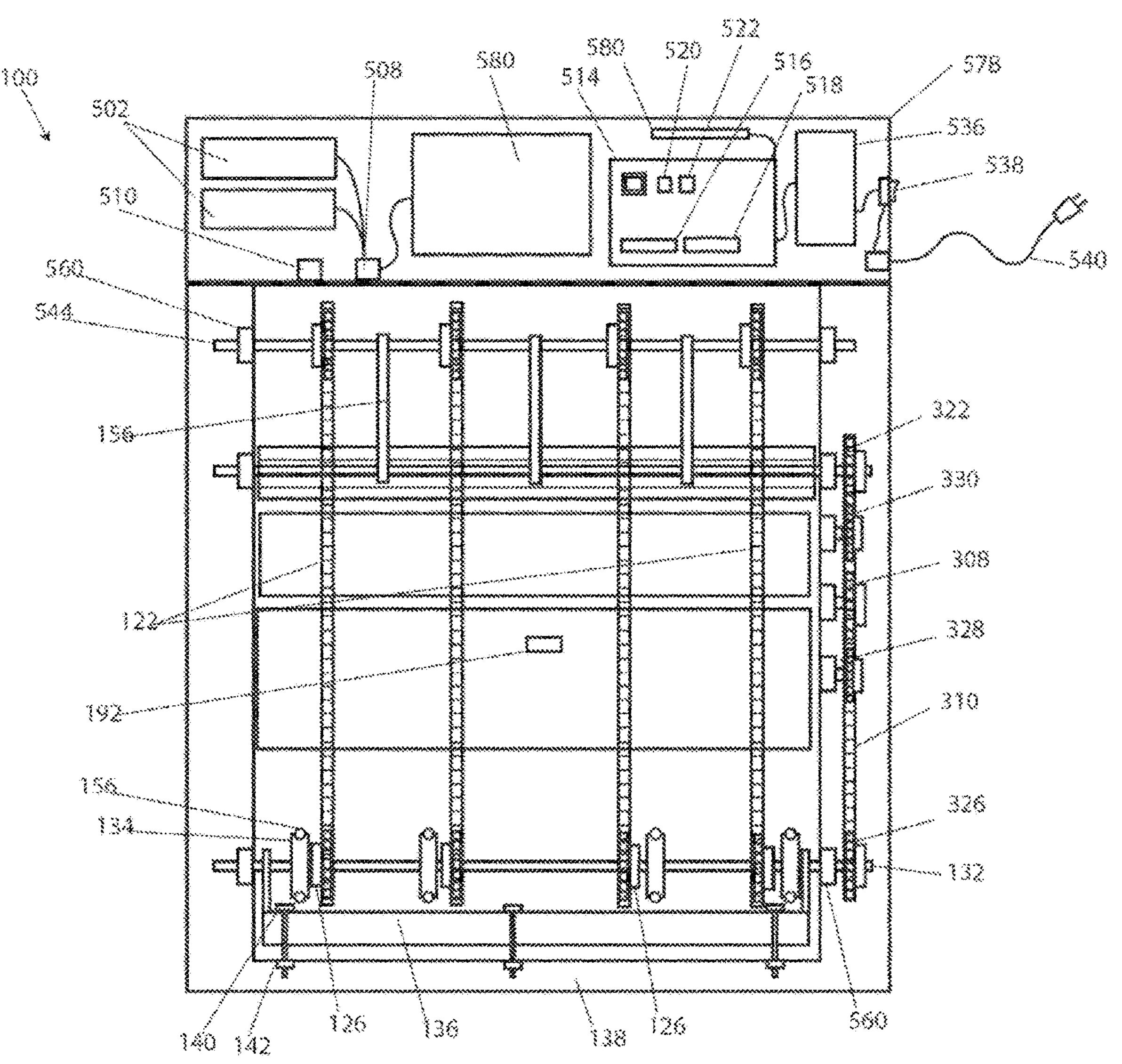
FIG. 5 illustrates a rear view of the example mat cleaner.

FIG. 5 illustrates a rear view of the example mat cleaner 100. The UVC Lamp Ballast 502 is an electronic device used to energize the lamp coils to vaporize mercury amalgam inside the lamp coils and excite the associated atoms to produce UVC light preferably in the 230 nm frequency typical of UVC light. UVC Lamp Ballast 502 preferably works with 120 VAC. The mat cleaner 100 detects when a lamp 130 is faulty and triggers a UVC lamp ballast failure event/error.

The ballast relay 508 is used to control the 120 VAC lamp ballasts, preferably with a 24 VOC output from the PCB 514. The spray pump relay 510 is preferably used to activate one or more 120 VAC pumps with a 24 VOC output from the PCB 514. The electronics control box 188 controls a PCB 514, microprocessor, input devices (sensors, microswitches, touchscreen) and output devices (relays, motor, pumps, lights, screen).

The PCB 514 supports the electro-mechanical components that make up the mat cleaner 100. The PCB 514 consists of input ports 516, output ports 518, an SD 520, and a SIM card 522. The input ports 516 are connected to sensors 518 and microswitches 520 that provide information to the PCB 514 regarding their current state. The PCB 514 can transmit data from the input ports 516 to a cloud-based application for automated metrics reporting and quality control. The output ports 518 control the sprayer pumps 524, the water pump 526, the lamps 528, the door locks 530, and the motor 532. The SD card 520 houses images that are displayed on a touch screen 534. The SIM card 522 is preferably specific to each individual mat cleaner 100 and allows the mat cleaner 100 to communicate over the air via a cellular network.

A power supply 536 is a device used to power the electronics by preferably converting 120 VAC to 24 VDC. A power button 538 is preferably a manual switch to power the mat cleaner 100 on. A power plug 540 is a cable that connects the mat cleaner 100 to an electrical outlet.

Each sprocket 542 controls a shaft 544 of varying functionality, so the drive chain length and sprocket sizes of the drive chain system are predetermined to have an appropriate rpm. The drive chain 310 is powered by the motor 546 and controls the brushes 548, the driver rollers 550, the conveyor subsystem 120, and the rolling subsystem 554.

The ends of the shafts 544 that house upper sprockets 556 and lower sprockets 558 are installed into flange bearings 560 to allow for a smooth rotation. Flange bearings 560 are present throughout the mat cleaner 100 and provide the shafts 544 a frictionless surface to rotate in. Sprocket covers 562 prevent a mat from getting stuck between the conveyor chain 564 and the teeth 566 of the lower sprockets 558.

The conveyor chains 564 are threaded around the upper sprockets 556 and lower sprockets 558, causing them to rotate when the drive train system 568 is activated and engages the rolling mechanism sprocket 569. The pulleys 134 and round belts 156 on the lower shaft 570 of the conveyor subsystem 120 are part of the rolling subsystem 574.

When the mat 106 is conveyed through the mat cleaner 100, and the mat 106 passes the optical sensor 192, the hydraulics subsystem 177 is activated. Similarly, the hydraulics system 177 is deactivated when the tail end of a mat 106 passes the optical sensor 192. If the optical sensor 192 does not detect a mat 106 after a predetermined amount of time once the cleaning cycle has begun, this may indicate a mat jam, and the mat 106 may be automatically reversed.

Aside from controlling the systems within the mat cleaner 100, the electronics control box 578 includes a cell antenna 580 that allows the mat cleaner 100 to communicate with the cellular network. The cellular connection allows for pushing firmware updates over the air along with reporting any data pertaining to usage or faults.

The electronics controls box 578 includes a touch screen display 580 which allows users to interact with the mat cleaner 100. For example, the touch screen display 580 can be an iPad, Android, or any other suitable screen. No credit card, barcode scan, or cash is necessarily needed to activate the mat cleaner 100 or pay for cleans. Instead, users may enter their phone number and pin on the touch screen display 580. Additionally, on the touch screen display 580, the user may see updates about the progress of the cleaning cycle and/or targeted ads. A maintenance screen and an admin screen may also be accessed via the touch screen display 580 with a series of predestined clicks and/or a secret password preferably only available to certain individuals. The maintenance screen allows an individual to manually control certain machine functions such as forward, reverse, priming, recirculation, and unlocking the door. The admin screen allows an individual to put a mat cleaner 100 in a test start mode, see the firmware version, flash a USB drive, etc.

Figure 6:
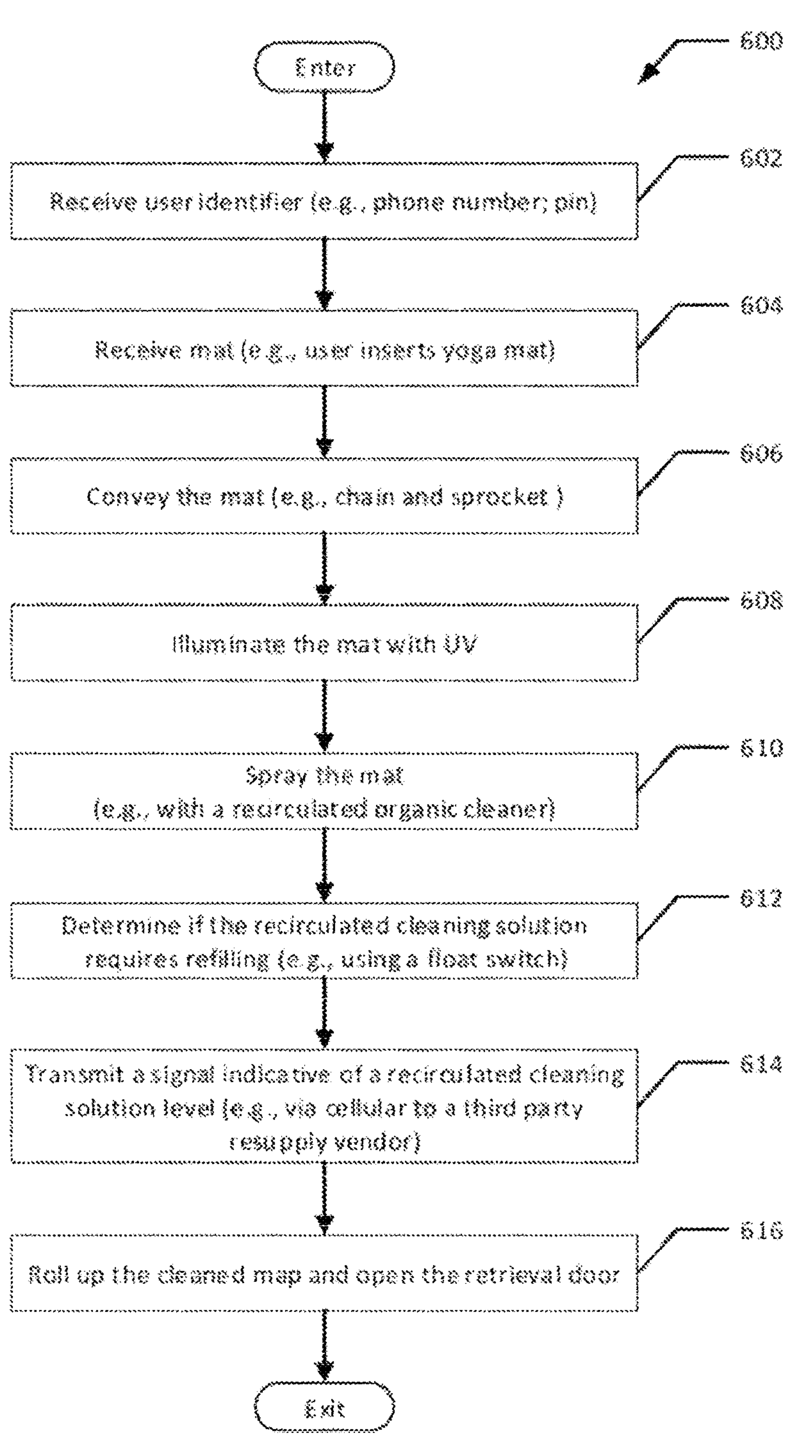
FIG. 6 is a flowchart of an example process for cleaning a mat using the mat cleaner.

FIG. 6 is a flowchart of an example process 600 for processing mats. Although the process 600 is described with reference to the flowchart illustrated in FIG. 6, it will be appreciated that many other methods of performing the acts associated with process 600 may be used. For example, the order of many of the operations may be changed, and some of the operations described may be optional.

In this example, the process 600 begins by receiving a user identifier. For example, a user may enter a phone number and/or a personal identification number (PIN) (block 602). The mat cleaner 100 then receives the mat 106 (block 604). For example, the user may insert a yoga mat. The mat cleaner 100 then conveys the mat 106 (block 606). For example, a chain and sprocket conveyance system may be used. The mat cleaner preferably 100 removes dirt/debris with brushes. The mat cleaner 100 then illuminates the mat 106 with ultraviolet radiation (UV) (block 608). During conveyance, the mat cleaner 100 also sprays the mat 106 with a cleaner (block 610). For example, the mat cleaner 100 may spray the mat 106 with a recirculated organic cleaner. The mat cleaner 100 also determines if the recirculated cleaning solution requires refilling (block 612). For example, a float switch may be used to facilitate determining a fluid level of the recirculated cleaning solution. The mat cleaner 100 may transmit a signal indicative of the recirculated cleaning solution level (block 614). For example, the recirculated cleaning solution level may be transmitted via cellular to a third party resupply vendor. After the mat 106 is cleaned, the mat cleaner 100 preferably rolls up the cleaned mat and automatically opens the retrieval door (block 616).

Referring now to FIGS. 7-12, a mat cleaner 101 consistent with another embodiment of the present disclosure includes an inlet 1101, a UV irradiation module 1200, and a mat rolling module 1600. Devices consistent with this embodiment generally provide enhanced feeding of mats to be cleaned, sanitize more thoroughly by UV light (e.g., irradiate more of the mat's surfaces with UV light), and provide more reliable rolling of the sanitized mat, regardless of the dimensions and thickness of the mat.

Figure 7:
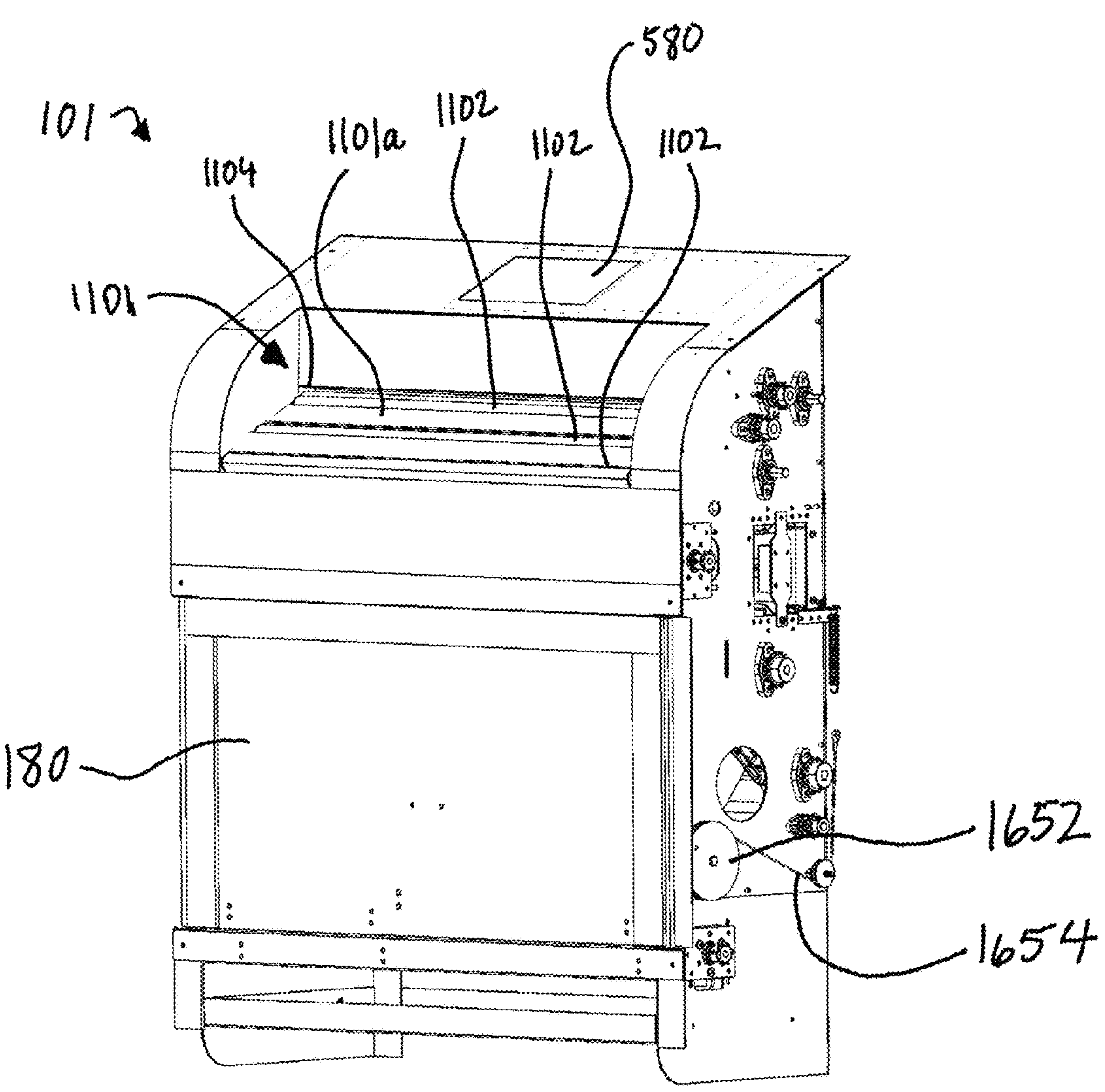
FIG. 7 shows a front perspective view of another example mat cleaner consistent with another embodiment of the present disclosure with a side panel removed to expose certain aspects of the embodiment.
Figure 8:
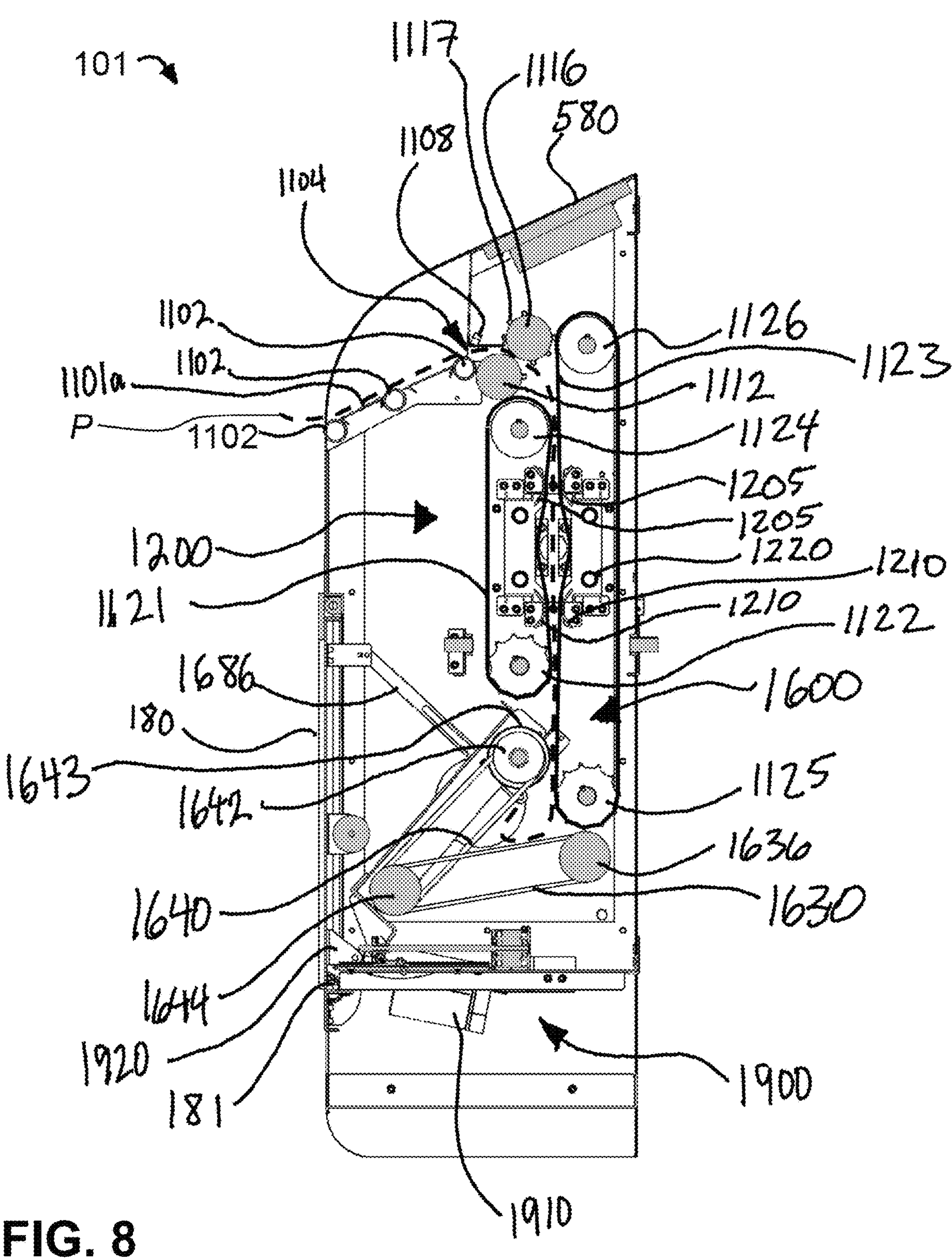
FIG. 8 shows a side cross-sectional view of the example mat cleaner of FIG. 7.

As shown in FIG. 7, the mat cleaner 101 includes an inlet 1101 configured to enable a user to feed a mat (not shown) along pathway P into the device. In some embodiments, the inlet 1101 includes one or more feed rollers 1102 configured to reduce resistance from friction between the mat and the surface 1101*a* of the inlet 1101. The feed rollers 1102 may be passive in some embodiments, while in other embodiments the feed rollers 1102 may be powered by one or more motors to actively draw the mat into the inlet gap 1104.

In some embodiments, the inlet 1101 includes one or more inlet rollers 1102 associated with an inlet platform 1101*a*. Generally, the one or more inlet rollers 1102 are disposed to assist the user to align the mat M with and guide the mat M into the inlet gap 1104. Each inlet roller 1102, when present, is disposed such that its axis (about which the roller rotates) is parallel with the width of the inlet gap 1104. In some embodiments, the inlet 1101 includes one inlet roller 1102. In another embodiment, the inlet 1101 includes two inlet rollers 1102. In other embodiments, the inlet 1101 includes three inlet rollers 1102. In still other embodiments, the inlet 1101 includes more than three inlet rollers 1102.

One or more sensors 1108 disposed adjacent the inlet gap 1104 may be present to, for example, determine the presence of and/or proper alignment of the mat's leading edge with the front driver roller 1112. The sensors 1108, when present, may also be configured to activate the mat cleaner 101, for example to cause the front driver roller 1112 and/or the rear driver roller 1116 to begin to rotate. In some embodiments, the one or more sensors 1108 are configured to cause the front driver roller 1112 and/or the rear driver roller 1116 to stop rotating after the mat passes completely beyond the sensors 1108. In some embodiments, the one or more sensors 1108 are configured to prevent (e.g., cause the display 580 to indicate a warning and/or prevent the front driver roller 1112 and/or the rear driver roller 1116 from rotating) if the mat is fed into the inlet gap 1104 in a crooked orientation. In some embodiments, the one or more sensors 1108 are not present.

A rear driver roller 1116 may be disposed beyond front driver roller 1112 and may be configured to drive the tail edge of the mat. In some embodiments, the rear driver roller 1116 includes one or more brush attachments 1117 extending at least a portion of the length of the rear driver roller 1116 and configured to remove detritus from the mat M. In some embodiments, each brush attachment 1117 extends from the surface of the rear driver roller 1116 the same distance (e.g., each brush attachment has the same height). In other embodiments, at least one brush attachment 1117 extends from the surface of the rear driver roller 1116 a greater distance (e.g., has a greater height than) at least one other brush attachment 1117. Without wishing to be bound by theory, it is currently believed that brush attachments 1117 extending multiple different distances from the surface of the rear driver roller 1116 may improve purchase of the driver rollers 1112, 1116 on the leading edge of relatively thin mats M as such mats M are guided into the inlet gap 1104.

The mat M is conveyed from the inlet gap 1104 to the UV irradiation module 1200 by one or more belts 1121, 1123. In some embodiments, the drive belts 1121, 1123 are substantially transparent to UV light. For example and without limitation, the drive belts 1121, 1123 may consist of, consist essentially of, or comprise a mesh material, such as a metal mesh or metal screen.

The one or more belts 1121, 1123 are driven by one or more drive rollers 1122, 1124. Each drive roller 1122, 1124 may be rotated in association with one or more motors.

In some embodiments, the mat M is conveyed from the inlet gap 1104 to the UV irradiation module 1200 by a first belt 1121 and a second belt 1123 disposed opposite the first belt 1121 relative to the pathway P. The first belt 1121 is driven by a first drive roller 1122. A first passive roller 1124 associated with the first belt 1121 is disposed opposite the first drive roller 1122. The second belt 1123 is driven by a second drive roller 1125. A second passive roller 1126 associated with the second belt 1123 is disposed opposite the second drive roller 1125. In some embodiments, a motor causes the first drive roller 1122 to rotate opposite the direction of the second drive roller 1125 such that the mat M is drawn downward through the UV irradiation module 1200 between the first belt 1121 and the second belt 1123.

The UV irradiation module 1200 is disposed along the pathway P between the first and second drive rollers 1122, 1125 and the first and second passive rollers 1124, 1126, and is configured to irradiate both the top surface of the mat and the bottom surface of the mat M simultaneously. The UV irradiation module 1200 of this example mat cleaner 101 provides a reliable and consistent distance between the UV light sources and the surfaces of the mat.

The UV irradiation module 1200 generally includes an entrance aperture 1206 and an exit aperture 1211 along the pathway P. The entrance aperture 1206 and exit aperture 1211 are configured to position the top surface and the bottom surface of the mat a consistent distance from the 1220.

Figure 11:
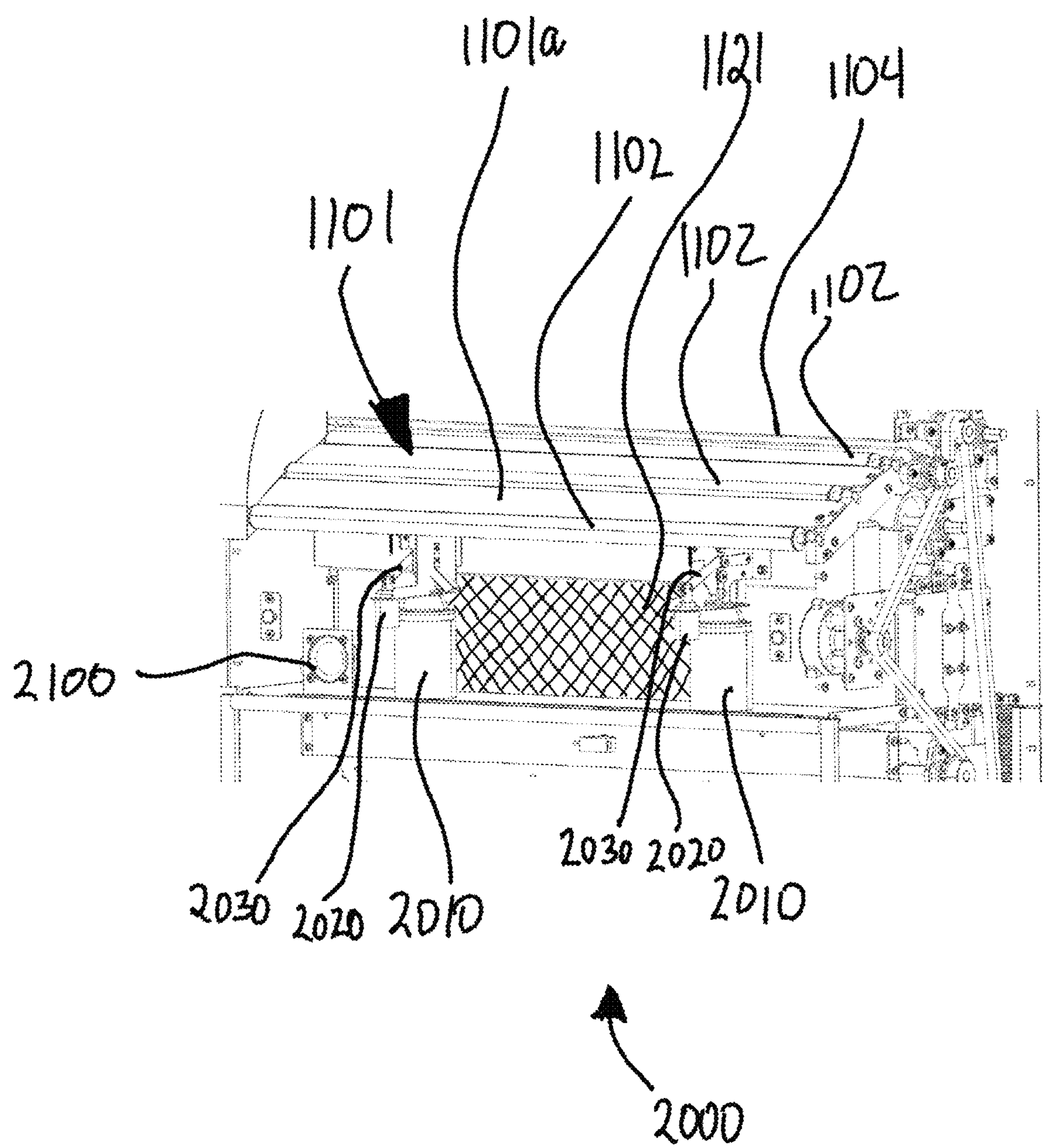
FIG. 11 shows a front perspective view of a portion of the mat cleaner of FIG. 7 with the front panel removed to show certain aspects of the embodiment.

The entrance aperture 1206 is formed by a pair of opposing channel guides 1205 (best shown in FIG. 11). The entrance aperture 1206 is at least 6 mm, at least 7 mm, at least 8 mm, at least 9 mm, at least 10 mm, at least 11 mm, or at least 12 mm. In some embodiments, the channel guides 1205 define a feed aperture 1207 that is larger than the entrance aperture 1206. In such embodiments, the wider feed aperture 1207 improves reliable feeding of the leading edge of the mat into the UV irradiation module 1200.

The UV irradiation module 1200 also includes an exit aperture 1211 formed by a pair of opposing channel guides 1210 (FIG. 11). The exit aperture 1211 is at least 6 mm, at least 7 mm, at least 8 mm, at least 9 mm, at least 10 mm, at least 11 mm, or at least 12 mm. In some embodiments, the entrance aperture 1206 and the exit aperture 1211 are the same dimension. In some embodiments, the channel guides 1210 define a feed aperture 1212 that is larger than the exit aperture 1211. In such embodiments, the relatively wider feed aperture 1212 improves reliable feeding of the leading edge of the mat into the exit aperture 1211.

In some embodiments, the UV irradiation module 1200 also includes a first belt deflector 1230 disposed between the first drive belt 1121 and the pathway P and configured to create a first gap 1231 between the first drive belt 1121 and the mat Mas the mat M is illuminated with UV light by the UV bulbs 1220. In such embodiments, relatively more UV light radiation contacts the surface of the mat M due to a reduction in shadows created by the first drive belt 1121. In some embodiments, the first belt deflector 1230 is a pair of first belt deflectors 1230 disposed at opposite ends of the UV irradiation module 1200. In some embodiments, each first belt deflector 1230 has a length of not more than 6 inches, such as not more than about 6 inches, not more than about 5.9 inches, not more than about 5.8 inches, not more than about 5.7 inches, not more than about 5.6 inches, not more than about 5.5 inches, not more than about 5.4 inches, not more than about 5.3 inches, not more than about 5.2 inches, not more than about 5.1 inches, not more than about 5 inches, not more than about 4.9 inches, not more than about 4.8 inches, not more than about 4.7 inches, not more than about 4.6 inches, not more than about 4.5 inches, not more than about 4.4 inches, not more than about 4.3 inches, not more than about 4.2 inches, not more than about 4.1 inches, not more than about 4 inches, not more than about 3.9 inches, not more than about 3.8 inches, not more than about 3.7 inches, not more than about 3.6 inches, not more than about 3.5 inches, not more than about 3.4 inches, not more than about 3.3 inches, not more than about 3.2 inches, not more than about 3.1 inches, not more than about 3 inches, not more than about 2.9 inches, not more than about 2.8 inches, not more than about 2.7 inches, not more than about 2.6 inches, not more than about 2.5 inches, not more than about 2.4 inches, not more than about 2.3 inches, not more than about 2.2 inches, not more than about 2.1 inches, not more than about 2 inches, not more than about 1.9 inches, not more than about 1.8 inches, not more than about 1.7 inches, not more than about 1.6 inches, not more than about 1.5 inches, not more than about 1.4 inches, not more than about 1.3 inches, not more than about 1.2 inches, not more than about 1.1 inches, not more than about 1 inch, not more than about 0.9 inches, not more than about 0.8 inches, not more than about 0.7 inches, not more than about 0.6 inches, or not more than about 0.5 inches.

In some embodiments, the UV irradiation module 1200 also includes a second belt deflector 1232 disposed between the second drive belt 1123 and the pathway P and configured to create a second gap 1233 between the second drive belt 1123 and the mat M as the mat M is illuminated with UV light by the UV bulbs 1220. In such embodiments, relatively more UV light radiation contacts the surface of the mat M due to a reduction in shadows created by the second drive belt 1123. In some embodiments, the second belt deflector 1232 is a pair of second belt deflectors 1232 disposed at opposite ends of the UV irradiation module 1200. In some embodiments, each second belt deflector 1232 has a length of not more than 6 inches, such as not more than about 6 inches, not more than about 5.9 inches, not more than about 5.8 inches, not more than about 5.7 inches, not more than about 5.6 inches, not more than about 5.5 inches, not more than about 5.4 inches, not more than about 5.3 inches, not more than about 5.2 inches, not more than about 5.1 inches, not more than about 5 inches, not more than about 4.9 inches, not more than about 4.8 inches, not more than about 4.7 inches, not more than about 4.6 inches, not more than about 4.5 inches, not more than about 4.4 inches, not more than about 4.3 inches, not more than about 4.2 inches, not more than about 4.1 inches, not more than about 4 inches, not more than about 3.9 inches, not more than about 3.8 inches, not more than about 3.7 inches, not more than about 3.6 inches, not more than about 3.5 inches, not more than about 3.4 inches, not more than about 3.3 inches, not more than about 3.2 inches, not more than about 3.1 inches, not more than about 3 inches, not more than about 2.9 inches, not more than about 2.8 inches, not more than about 2.7 inches, not more than about 2.6 inches, not more than about 2.5 inches, not more than about 2.4 inches, not more than about 2.3 inches, not more than about 2.2 inches, not more than about 2.1 inches, not more than about 2 inches, not more than about 1.9 inches, not more than about 1.8 inches, not more than about 1.7 inches, not more than about 1.6 inches, not more than about 1.5 inches, not more than about 1.4 inches, not more than about 1.3 inches, not more than about 1.2 inches, not more than about 1.1 inches, not more than about 1 inch, not more than about 0.9 inches, not more than about 0.8 inches, not more than about 0.7 inches, not more than about 0.6 inches, or not more than about 0.5 inches.

The UV irradiation module 1200 includes at least two UV bulbs 1220. At least one UV bulb 1220 is disposed to illuminate a first surface M1 of the mat M, while at least one UV bulb 1220 is disposed to illuminate a second, opposite surface M2 of the mat M. In the specific embodiment shown in FIG. 9, for example, two UV bulbs 1220 are disposed to illuminate the first surface M1 of the mat M, while two UV bulbs 1220 are disposed to illuminate the second surface M2 of the mat M.

Figure 9:
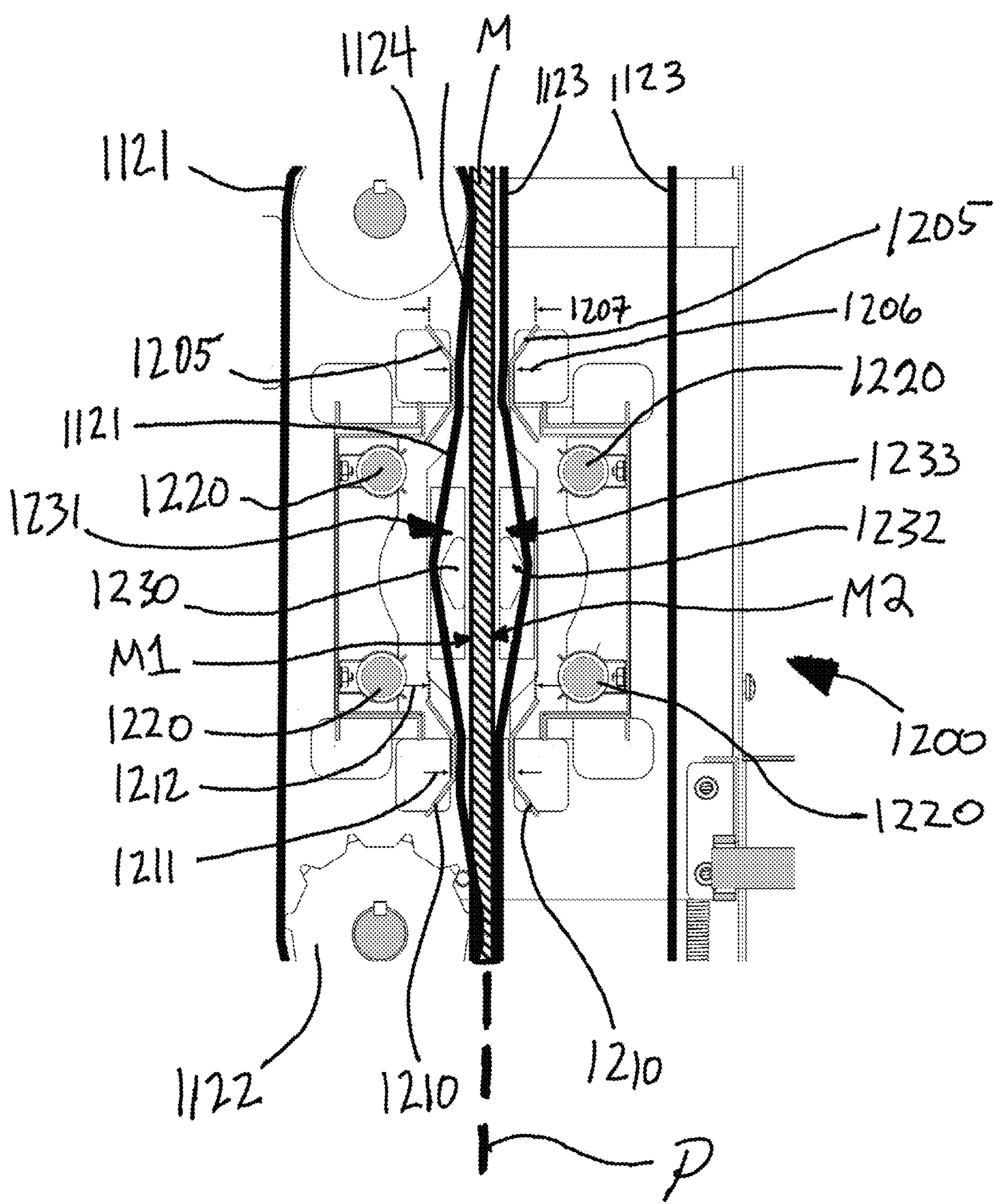
FIG. 9 shows an enlarged side cross-sectional view of the UV irradiation module of the mat cleaner of FIG. 7.
Figure 10:
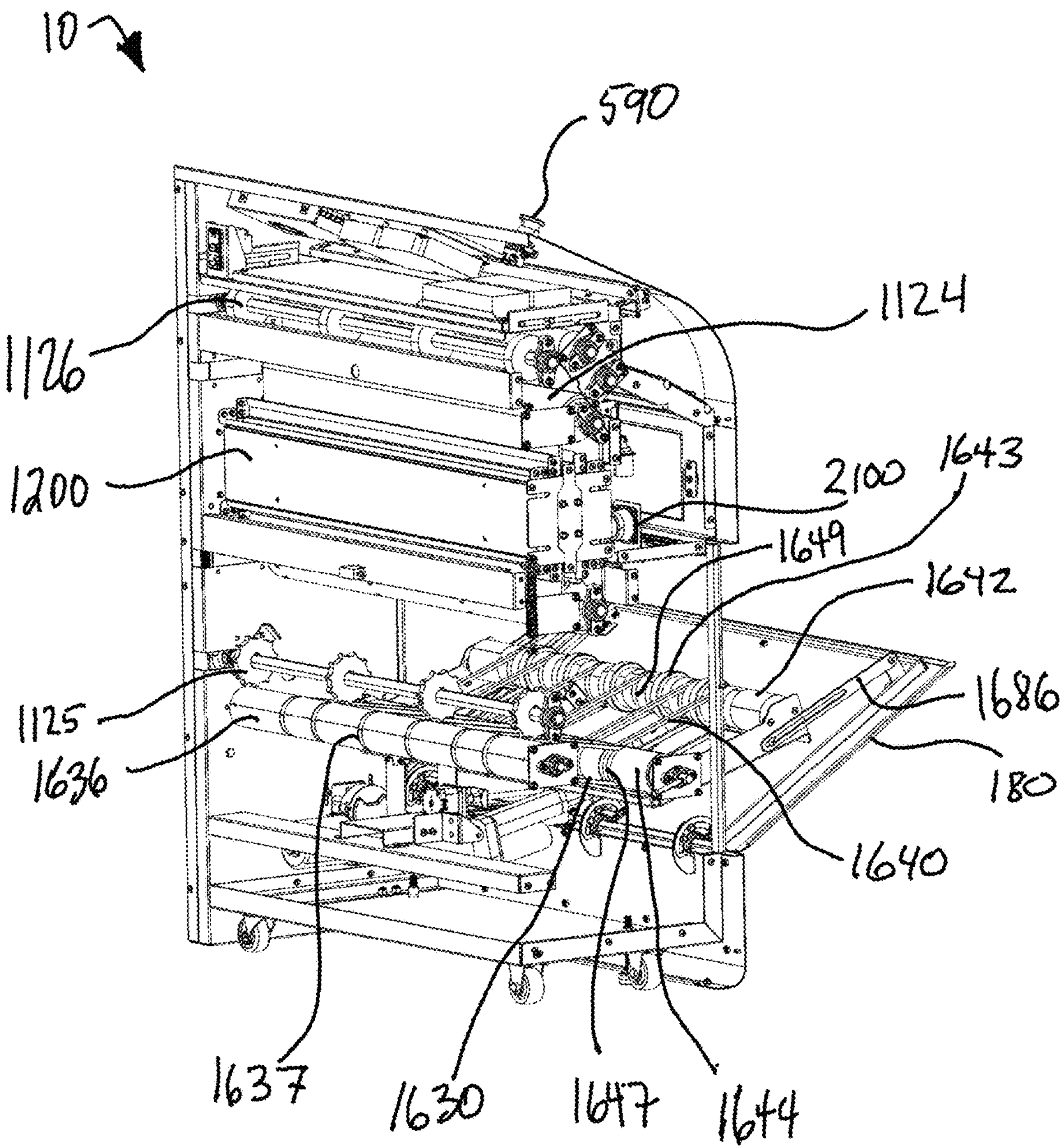
FIG. 10 shows a rear perspective view of the mat cleaner of FIG. 7 with the rear and side panels removed to expose certain aspects of the embodiment.

In some embodiments, including those consistent with the specific embodiment shown in FIG. 9, the first belt 1121 is disposed between the mat M and at least one UV bulb 1220. In such embodiments, the first surface M1 of the mat M is illuminated by UV light that passes through the first belt 1121 and/or through gaps in the material comprising the first belt 1121.

In some embodiments, including those consistent with the specific embodiment shown in FIG. 9, the second belt 1123 is disposed between the mat M and at least one UV bulb 1220. In such embodiments, the second surface M2 of the mat M is illuminated by UV light that passes through the second belt 1123 and/or through gaps in the material comprising the first belt 1123.

In some embodiments, at least one UV bulb is disposed within the first gap 1231 (e.g., between the first belt 1121 and the first surface M1 of the mat M.

In some embodiments, at least one UV bulb is disposed within the second gap 1233 (e.g., between the second belt 1123 and the second surface M2 of the mat M.

The mat cleaner 101 may be configured to advance the mat through the UV irradiation module 1200 at a rate sufficient to expose any one point of the top or bottom surface of the mat to UV irradiation for not more than 10 seconds, for example not more than 10 seconds, not more than 9 seconds, not more than 8 seconds, not more than 7 seconds, not more than 6 seconds, not more than 5 seconds, not more than 4 seconds, not more than 3 seconds, not more than 2 seconds, or not more than 1 second.

A feed roller 1122 may be disposed adjacent the exit aperture 1211 to advance the leading edge of the mat to the rolling module 1600.

The rolling module 1600 is disposed along the pathway P beyond the UV irradiation module 1200 and is configured to roll the sanitized mat into a roll for convenient removal from the mat cleaner 101. In general, the rolling module 1600 includes a first rolling belt 1630 and a second rolling belt 1640 that each work in concert with each other and with at least a portion of the second belt 1123 to roll the mat M. Alternatively, the rolling module 1600 includes a first rolling belt 1630, a second rolling belt 1640, and a third rolling belt (not shown) not associated with the second belt 1123 that work in concert with each other to roll the mat M.

The first rolling belt 1630 is disposed proximal to the second belt 1123, and is configured to draw the leading edge of the mat M away from the second belt 1123. The first rolling belt 1630 is driven by a drive roller 1644 and passes over a passive roller 1636. In some embodiments, the drive roller 1644 includes a groove 1647 into which each band of the first rolling belt 1630 is disposed. In some embodiments, the passive roller 1636 includes a groove 1637 into which each band of the first rolling belt 1630 is disposed.

The second rolling belt 1640 is disposed proximal to the first rolling belt 1630 and is configured to draw the leading edge of the mat M away from the first rolling belt 1630, back over the middle portion of the mat M, and towards the second belt 1123. The second roller belt 1640 is further disposed over a second passive roller 1642. In some embodiments, the second rolling belt 1640 is driven by a drive roller 1644. In the embodiment specifically illustrated in FIGS. 8-15, the first rolling belt 1630 and the second rolling belt 1640 are both powered by the same drive roller 1644. In some embodiments, the drive roller 1644 includes a groove 1647 into which each band of the second rolling belt 1640 is disposed. In some embodiments, the second passive roller 1642 includes a groove 1649 into which each band of the first rolling belt 1630 is disposed.

In some embodiments, the second passive roller 1642 includes one or more rings 1643 configured to contact the mat M as it is conveyed into the rolling area 1650 by the second belt 1123, for example to prevent the leading edge of the mat M from exiting the rolling area 1650. In such embodiments, each ring 1643 is configured to rotate about the second passive roller 1642 in a direction opposite the direction the second passive roller 1642 is caused to rotate by the second rolling belt 1640.

In some embodiments, the second rolling belt 1640 is disposed at an adjustable angle 1690 to the first rolling belt 1630. For example and without limitation, the second rolling belt 1640 may be disposed about a pivot coaxial with the drive roller 1644, while the associated passive roller 1642 is associated with a guide rail 1686. As the mat M rolls in the rolling area 1650, the second rolling belt 1640 may pivot away from the second belt 1123 to increase the adjustable angle 1690 and enlarge the rolling area 1690.

Figure 12:
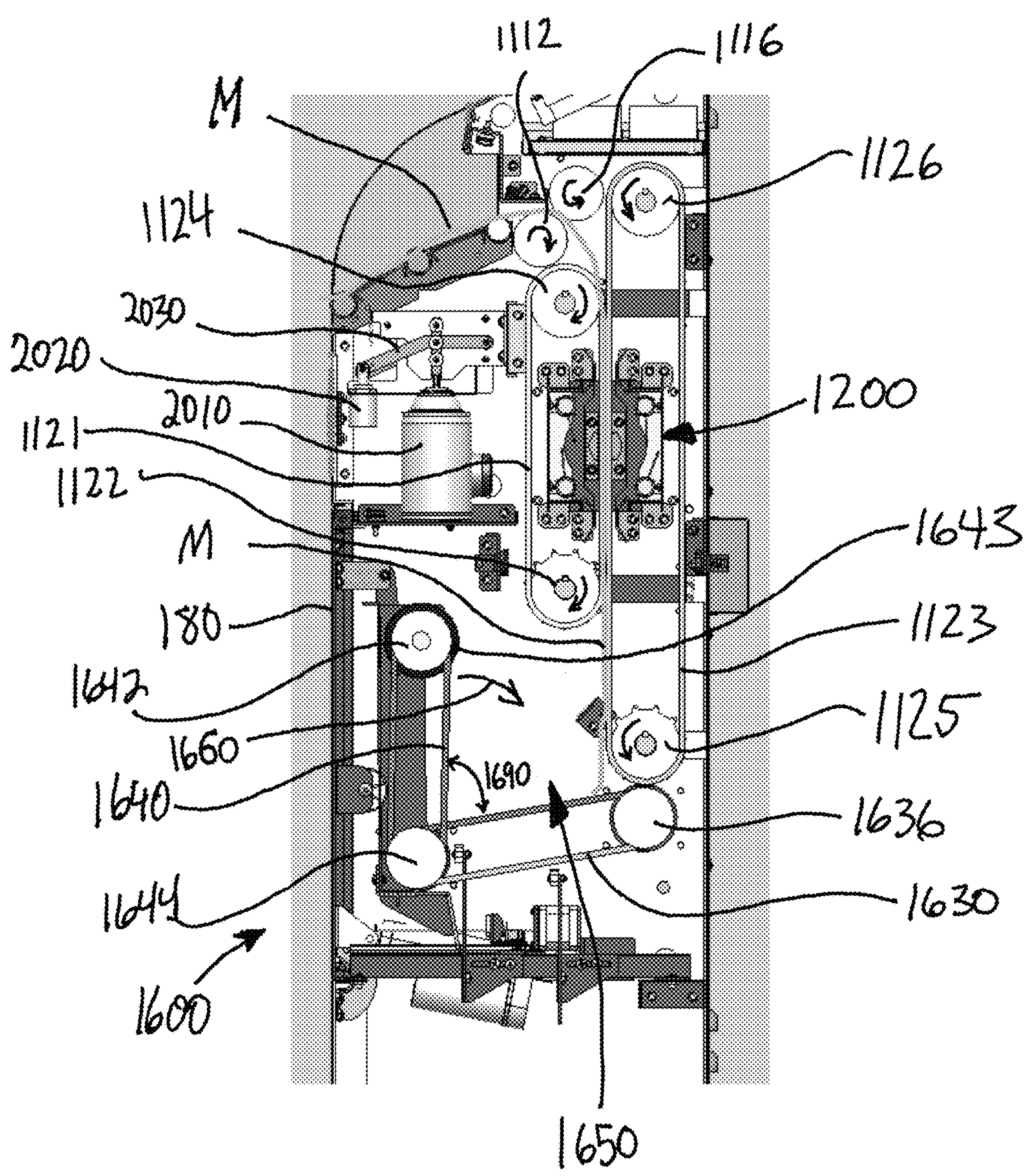
FIG. 12 shows a side cross-sectional view of a portion of the mat cleaner of FIG. 7 before rolling of the cleaned mat has begun.
Figure 13:
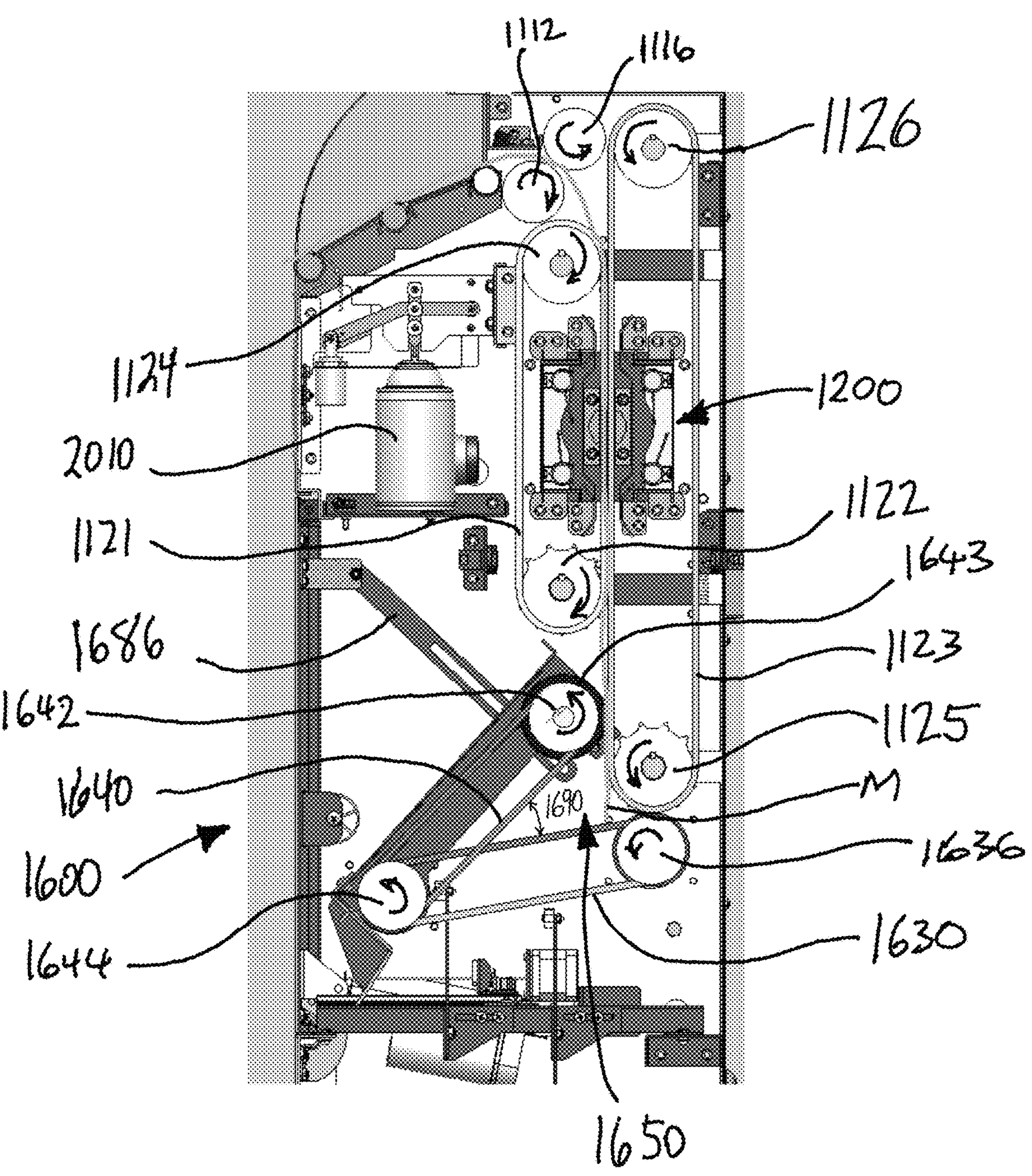
FIG. 13 shows a side cross-sectional view of a portion of the mat cleaner of FIG. 7 as rolling of the cleaned mat has already begun.
Figure 14:
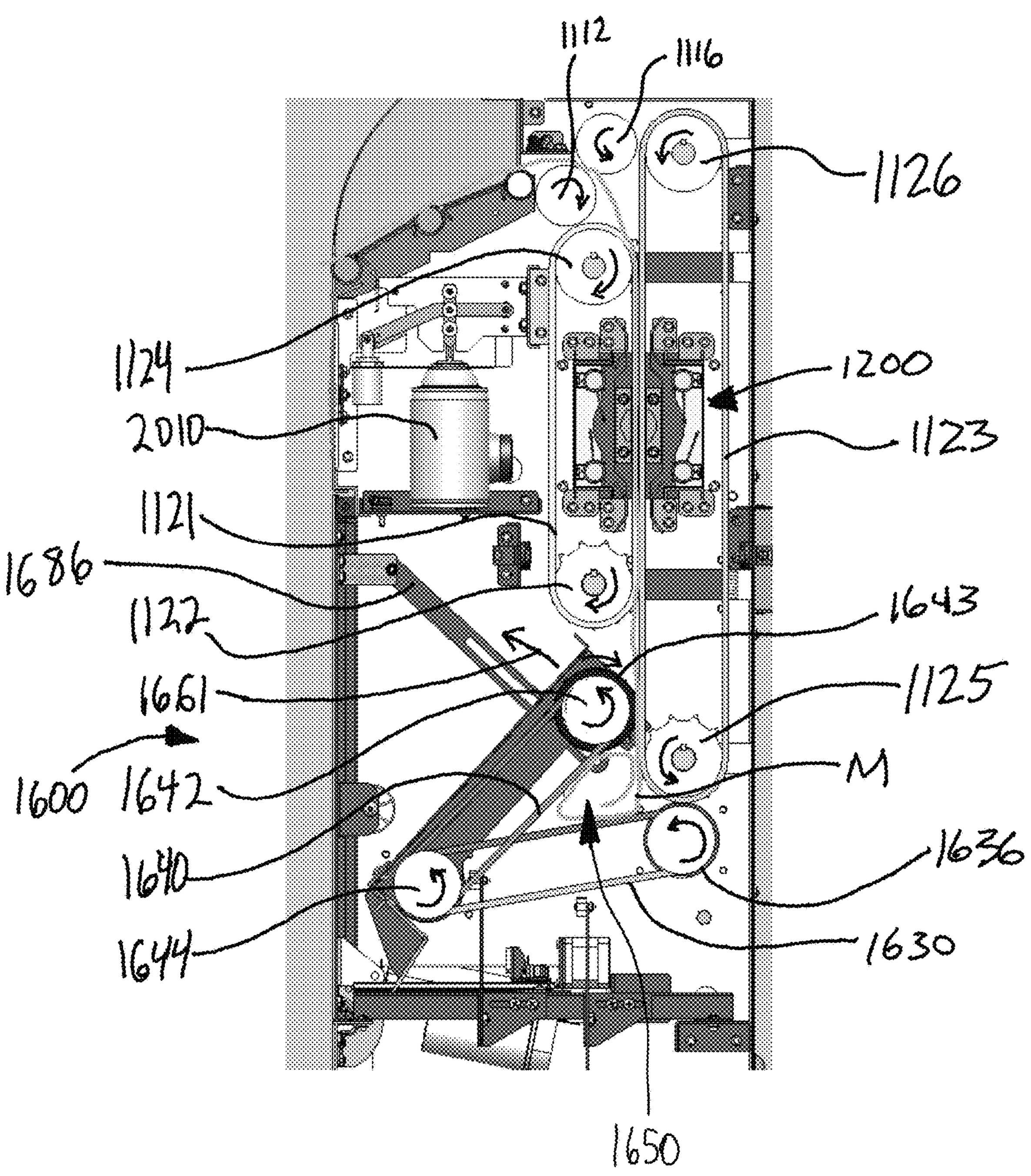
FIG. 14 shows a side cross-sectional view of a portion of the mat cleaner of FIG. 7 about halfway through rolling of the mat.
Figure 15:
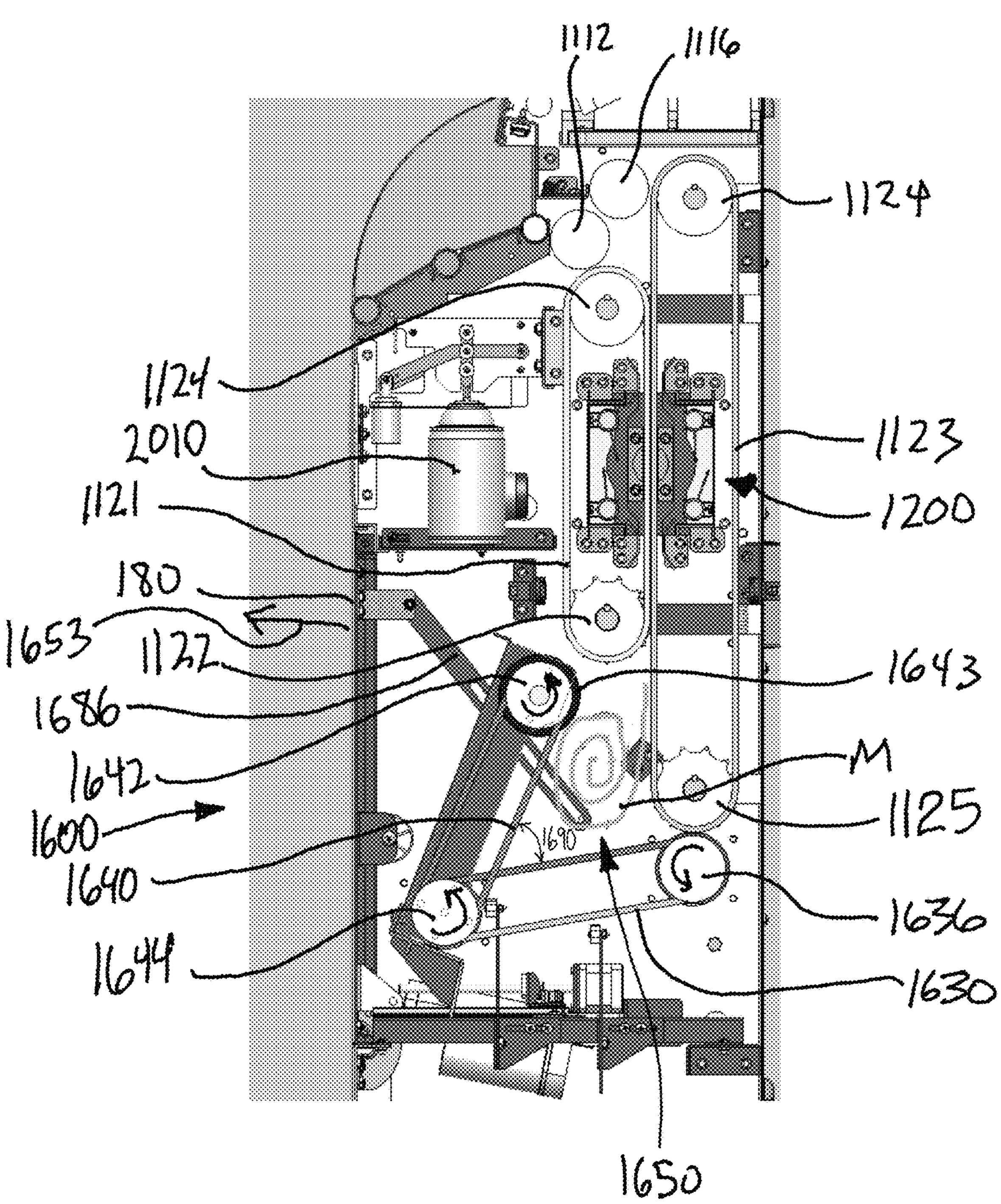
FIG. 15 shows a side cross-sectional view of a portion of the mat cleaner of FIG. 7 as rolling of the mat has nearly completed.

In operation, the rolling module 1600 may adopt an initial configuration with the adjustable angle 1690 at a maximum value, such as shown in FIG. 12, as the leading edge of the mat M enters the rolling area 1650. A sensor may be configured to detect the presence of the leading edge of the mat M within the rolling area 1650, which may cause the second rolling belt 1640 to rotate towards the second belt 1123, for example along arrow 1660, until the rings 1643 contact the mat M. A motor (not shown) may then engage to cause the drive roller 1644, the passive roller 1636, and the second passive roller 1642 to rotate in the directions illustrated in FIG. 13. The relative motions of the first rolling belt 1630, the second rolling belt 1640, and the second belt 1123 cause the mat M to roll on itself in the rolling area 1650. As the mat M continues to roll in the rolling area 1650, the increasing radius of the mat M causes the second rolling belt 1640 to rotate away from the second belt 1123, for example along arrow 1661 (FIG. 14). As the trailing edge of the mat M enters the rolling area 1650, the first drive roller 1122 and the second drive roller 1125 may stop rotating (e.g., in response to a sensor detecting the absence of the mat M proximal to the UV irradiation module 1200). After rolling of the mat M is complete (e.g., after a predetermined period of time after the mat M exits the UV irradiation module 1220), the drive roller 1644 may stop rotating.

The mat cleaner 101 may additionally be configured to cause the door 180 to open after (e.g., only after) the mat M is rolled by the rolling module 1600. In such embodiments, an automatic door module 1900 may be disposed adjacent the rolling module 1600 and generally includes an actuator 1910 and a door adapter 1920. The actuator 1910 is disposed adjacent the door 180 and is in mechanical communication with the door adapter 1920. The door adapter 1920 is associated with the door 180, for example near the door hinge 181. In operation, the actuator 1910 advances the door adapter 1920 to cause the door 180 to open about its hinge 181, enabling the use to retrieve the rolled mat M from the rolling module 1600. In some embodiments, the automatic door module 1900 is configured to prevent the door 180 from opening (e.g., being opened by a user) when the UV light sources are illuminated. In some embodiments, the door 180 opens in response to movement of a cable 1654 in tension with the door 180 and passing about an asymmetric pulley 1652.

In some embodiments, the mat cleaner 101 further includes an electronics control box 578 including a cell antenna enabling the mat cleaner 101 to communicate with a cellular network. The cellular connection allows for pushing firmware updates over the air along with reporting any data pertaining to usage or faults.

The electronics controls box 578 includes a touch screen display 580 which allows users to interact with the mat cleaner 101. For example, the touch screen display 580 can be an iPad, Android, or any other suitable screen. No credit card, barcode scan, or cash is necessarily needed to activate the mat cleaner 101 or pay for cleans. Instead, users may enter their phone number and pin on the touch screen display 580. Additionally, on the touch screen display 580, the user may see updates about the progress of the cleaning cycle and/or targeted ads. A maintenance screen and an admin screen may also be accessed via the touch screen display 580 with a series of predestined clicks and/or a secret password preferably only available to certain individuals. The maintenance screen allows an individual to manually control certain machine functions such as forward, reverse, priming, recirculation, and unlocking the door. The admin screen allows an individual to put a mat cleaner 101 in a test start mode, see the firmware version, flash a USB drive, etc. In some embodiments, the touch screen display 580 may additionally include, or be replaced by, an RF, Bluetooth, or visual code that enables the mat cleaner 101 to identify the user and optionally charge the user for cleans via the user's mobile device (e.g., smartphone or radio tag).

In some embodiments, the mat cleaner 101 does not include a brush (e.g., a roller brush) configured to remove dirt and/or debris from the surface(s) of the mat.

In some embodiments, the mat cleaner 101 includes one or more speakers 2100 in electrical communication with the electronics controls box 578 and configured to play an audio signal generated by the electronics controls box 578.

In some embodiments, the mat cleaner 101 includes a fragrance module 2000 configured to apply a fragrance to at least one surface of the mat M. For example and without limitation, the fragrance module 2000 may include one or more canisters 2010 configured to store a fragrance. The fragrance module 2000 also includes an actuator 2020 configured to cause the canister 2010 to propel fragrance toward the mat M. The actuator 2020 may be in operative communication with one or more levers or arms 2030 configured to activate the canister 2010 in response to the actuator 2020. In some embodiments, the actuator 2020 is in operative communication with a sensor configured to detect the presence (or absence) of the mat Min proximity to the fragrance module 2000. In some embodiments, the fragrance module 2000 is configured to apply fragrance to only one side (face) of the mat M. In other embodiments, the fragrance module 2000 is configured to apply fragrance to both sides (faces) of the mat M. Although the fragrance module 200 is shown disposed opposite the first belt 1121 from the mat M in the embodiment specifically illustrated in FIGS. 8 and 11, the fragrance module 2000 may be disposed at any suitable location along the pathway P to apply fragrance to the mat M.

In some embodiments, the mat cleaner 101 includes a sensor (not shown) configured to detect when the leading edge of the mat M deviates from the pathway P, for example by rolling around the front driver roller 1112 or the rear driver roller 1116. In some embodiments, such sensor is in operable communication with the control box 578, which may be configured to cause the speaker(s) 2100 to sound an alert and/or to cause the display 580 to indicate a fault state associated with the mat's deviation from the pathway P.

In some embodiments, the mat cleaner 101 includes an emergency stop button 590 in operable communication with the control box 578 and configured to enable a user to stop or interrupt the operation of the mat cleaner 101, for example if the mat M is being drawn into the inlet 1104 askew. In some embodiments, depressing the emergency stop button 590 causes the motor(s) driving the various rollers and belts to stop. In some embodiments, depressing the emergency stop button 590 causes the motor(s) driving the various rollers and belts to (a) stop driving the various rollers and belts, and (b) enter a neutral state that enables the user to retract the mat M from the inlet 1104 by pulling the trailing edge of the mat M away from the mat cleaner 101.

In some embodiments, the mat cleaner 101 does not include a module configured to apply a cleaning solution to the surface(s) of the mat.

In summary, persons of ordinary skill in the art will readily appreciate that methods and apparatus for cleaning a mat have been provided. The foregoing description has been presented for the purposes of illustration and description. It is not intended to be exhaustive or to limit the invention to the exemplary embodiments disclosed. Many modifications and variations are possible in light of the above teachings. It is intended that the scope of the invention be limited not by this detailed description of examples, but rather by the claims appended hereto.

EXAMPLES

Example 1

Yoga mats of various shapes and thicknesses were cleaned using a mat cleaner 101 consistent with the embodiment specifically shown in FIGS. 7-12.

Thirty-one types of dry and damp yoga mats were fed into the example mat cleaner 101 multiple times each to gauge reliability of insertion, reliability of rolling, and reliability of the automatic door open feature. Results of 740 test iterations are shown in Table 1.

TABLE 1

| Dry and Damp Mats | | | | | | |
|---|---|---|---|---|---|---|
| Mat Brand | n | Insertion Feed Success Rate | Door Open Success Rate | Roll Success Rate | Roll Major Telescope Rate | Center |
| Jeis Yoga | 20[(a)] | 100% | 100% | 100% | 5% | O[(d)] (100%) S[(e)] (0%) |
| Manduka (A) | 20[(a)] | 100% | 100% | 100% | 0% | O (100%) S (0%) |
| EKO (A) | 20[(a)] | 100% | 100% | 100% | 10% | O (50%) S (45%) Other (5%) |
| EKO (B) | 20[(a)] | 100% | 100% | 100% | 0% | O (75%) S (25%) |
| EKO (C) | 20[(a)] | 100% | 100% | 100% | 0% | O (75%) S (25%) |
| Unknown (A) | 40[(b)] | 100% | 100% | 100% | 2.5% | O (55%) S (42.5%) Other (2.5%) |
| Jade Yoga (A) | 20[(a)] | 100% | 100% | 100% | 0% | O (90%) S (0%) Other (10%) |
| Jade Yoga (B) | 20[(a)] | 100% | 100% | 100% | 0% | O (75%) S (25%) |
| Polyopic | 20[(a)] | 100% | 100% | 100% | 10% | O (50%) S (50%) |
| Alo | 20[(a)] | 90% | 100% | 100% | 5% | O (50%) S (50%) |
| Unknown (B) | 40[(b)] | 100% | 100% | 100% | 2.5% | O (50%) S (50%) |
| Unknown (C) | 20[(a)] | 100% | 100% | 100% | 0% | O (75%) S (25%) |
| Cevo Yoga | 20[(a)] | 100% | 100% | 100% | 20% | O (70%) S (30%) |
| Unknown (D) | 20[(a)] | 100% | 100% | 100% | 10% | O (70%) S (30%) |
| Unknown (E) | 20[(a)] | 100% | 100% | 100% | 0% | O (60%) S (15%) Other (25%) |

TABLE 1-continued

| Dry and Damp Mats | | | | | | |
|---|---|---|---|---|---|---|
| Mat Brand | n | Insertion Feed Success Rate | Door Open Success Rate | Roll Success Rate | Roll Major Telescope Rate | Center |
| Manduka (B) | 20[a] | 100% | 100% | 100% | 5% | O (90%) S (10%) |
| Unknown (F) | 20[a] | 100% | 100% | 100% | 5% | O (35%) S (25%) Other (40%) |
| EKO (D) | 20[a] | 95% | 100% | 100% | 10% | O (100%) S (0%) |
| Jade Yoga (C) | 20[a] | 100% | 100% | 100% | 10% | O (70%) S (30%) |
| Unknown (G) | 20[a] | 95% | 100% | 100% | 5% | O (70%) S (10%) Other (20%) |
| Unknown (H) | 20[a] | 100% | 100% | 100% | 5% | O (50%) S (50%) |
| Gaiam (A) | 20[a] | 100% | 100% | 100% | 10% | O (35%) S (40%) Other (25%) |
| Prana | 40[b] | 100% | 100% | 100% | 12.5% | O (70%) S (27.5%) Other (2.5%) |
| Unknown (I) | 40[b] | 100% | 100% | 100% | 20% | O (52.5%) S (47.5%) |
| Unknown (J) | 20[a] | 100% | 100% | 100% | 5% | O (50%) S (50%) |
| Nike | 20[a] | 90% | 100% | 100% | 0% | O (100%) S (0%) |
| Unknown (K) | 40[b] | 100% | 100% | 100% | 15% | O (50%) S (50%) |
| Unknown (L) | 40[b] | 100% | 100% | 100% | 15% | O (45%) S (52.5%) Other (2.5%) |
| Gaiam (B) | 20[a] | 100% | 100% | 100% | 5% | O (50%) S (50%) |
| Life Energy | 20[a] | 100% | 100% | 100% | 15% | O (55%) S (45%) |
| Liforme | 20[a] | 80% | 100% | 100% | 25% | O (50%) S (45%) Other (5%) |
| TOTAL/AVG. | 740[c] | 98.6% | 100% | 100% | 8.0% | O (64.0%) S (32.0%) Other (4.0%) |

[a]All mats tested were dry to the touch.

[b]Half of the mats tested were dry to the touch; half of the mats tested were damp.

[c]620 mats tested were dry to the touch; 120 mats tested were damp.

[d]"O" indicates that the innermost ring of the rolled yoga mat is an uninterrupted and cylindrical lumen.

[e]"S" indicates that the innermost ring of the rolled yoga mat includes serpentine-shaped layer of yoga math through the lumen.

These data show that the mat cleaner 101 provides reliable automated insertion, rolling, and triggering of an automated door open feature regardless of the yoga mat's quality, dimension, or thickness.

Six types of damp yoga mats were fed into the example mat cleaner 101 multiple times each to gauge reliability of insertion, reliability of rolling, and reliability of the automatic door open feature. Results of 120 test iterations are shown in Table 2.

TABLE 2

| Damp Mats Only | | | | | | |
|---|---|---|---|---|---|---|
| Mat Brand | n | Insertion Feed Success Rate | Door Open Success Rate | Roll Success Rate | Roll Major Telescope Rate | Center |
| Unknown (A) | 20 | 100% | 100% | 100% | 5% | O[(a)] (35%) S[(b)] (60%) Other (5%) |
| Unknown (B) | 20 | 100% | 100% | 100% | 5% | O (50%) S (50%) |
| Prana | 20 | 100% | 100% | 100% | 10% | O (40%) S (55%) Other (5%) |
| Unknown (I) | 20 | 100% | 100% | 100% | 35% | O (50%) S (50%) |
| Unknown (K) | 20 | 100% | 100% | 100% | 5% | O (50%) S (50%) |
| Unknown (L) | 20 | 100% | 100% | 100% | 5% | O (40%) S (55%) Other (5%) |
| TOTAL/AVG. | 120 | 100% | 100% | 100% | 10.8% | O (44.2%) S (53.3%) Other (2.5%) |

[(a)] "O" indicates that the innermost ring of the rolled yoga mat is an uninterrupted and cylindrical lumen.
[(b)] "S" indicates that the innermost ring of the rolled yoga mat includes serpentine-shaped layer of yoga mat through the lumen.

These data show that the mat cleaner 101 provides reliable automated insertion, rolling, and triggering of an automated door open feature regardless of the yoga mat's quality, dimension, or thickness.

I claim:

1. A device for cleaning a mat, the device comprising:
an inlet feed system configured to draw a mat into the device;
an ultraviolet irradiation module configured to sanitize the mat, the ultraviolet irradiation module comprising:
a first belt,
a second belt disposed opposite the first belt, and
at least one ultraviolet lamp disposed between the first and second belts;
wherein the first and second belts are configured to draw a leading edge of the mat from the inlet feed system towards the at least one ultraviolet lamp;
a rolling module configured to roll the sanitized mat into a roll, the rolling module comprising:
a first rolling belt configured to draw the leading edge of the mat from the second belt of the ultraviolet irradiation module towards a front side of the device, and
a second rolling belt disposed at an adjustable angle to the first rolling belt and configured to draw the leading edge of the mat away from the first rolling belt and towards the second belt of the ultraviolet irradiation module; and
an automatic door actuator configured to selectively prevent a door from opening and to open the door.

2. The device of claim 1 further comprising an electronics control box configured to identify a user of the device and to control the inlet feed system, the ultraviolet irradiation module, the rolling module, and the automatic door actuator.

3. The device of claim 1, wherein the inlet feed system includes a plurality of feed rollers configured to reduce resistance from friction between the mat and an external surface of the inlet feed system.

4. The device of claim 1, wherein the inlet feed system includes one or more sensors proximal to an inlet gap, the sensors configured to determine whether the mat is fed into the inlet gap straight or askew.

5. The device of claim 1, wherein the ultraviolet irradiation module comprises:
a first pair of opposing channel guides having:
a minimum gap therebetween defining an entrance aperture, and
a relatively larger gap therebetween defining an entrance feed aperture;
a second pair of opposing channel guides having:
a minimum gap therebetween defining an exit aperture, and
a relatively larger gap therebetween defining an exit feed aperture;
a first UV lamp disposed between the first and second pair of opposing channel guides and configured to illuminate a first surface of the mat as it passes between the first and second pair of opposing channel guides; and
a second UV lamp disposed between the first and second pair of opposing channel guides and configured to illuminate a second, opposite surface of the mat as it passes between the first and second pair of opposing channel guides.

6. The device of claim 1, wherein the ultraviolet irradiation module further comprises:
a first belt deflector configured to form a first gap between a first surface of the mat and the first belt; and
a second belt deflector configured to form a second gap between a second surface of the mat and the second belt.

7. The device of claim 2, wherein the automatic door actuator comprises:
a rod in association with the door; and
a linear actuator in operative communication with the electronics control box and configured to selectively advance and retract the rod.

8. The device of claim 7, wherein the electronics control box is configured to cause the linear actuator to retract the rod upon insertion of a mat into the inlet feed system.

9. The device of claim 7, wherein the electronics control box is configured to cause the linear actuator to not advance the rod while the ultraviolet irradiation module is activated.

10. The device of claim 7, wherein the electronics control box is configured to cause the linear actuator to not advance the rod while the rolling module is activated.

11. The device of claim 7, wherein the electronics control box is configured to cause the linear actuator to advance the rod after the rolling module has completed rolling the mat.

12. The device of claim 5, wherein:
the inlet feed system includes one or more sensors proximal to an inlet gap, the one or more sensors configured to determine whether the mat is fed into the inlet gap straight or askew; and
the electronics control box is configured to activate one or more feed rollers to transport the mat from the inlet feed system to the ultraviolet irradiation module in response to a signal from the one or more sensors that the mat is not fed into the inlet gap askew.

13. The device of claim 2, wherein the electronics control box is configured to activate the ultraviolet irradiation module only when the automatic control actuator is preventing the door from opening.

* * * * *